United States Patent
Tonouchi et al.

(10) Patent No.: US 6,316,251 B1
(45) Date of Patent: Nov. 13, 2001

(54) GENE, GROUP OF GENES, AND NOVEL β-GLUCLOSIDASE

(75) Inventors: Naoto Tonouchi; Takayasu Tsuchida, both of Kawasaki; Fumihiro Yoshinaga, Hujisawa; Naoki Tahara, Ibaraki; Hisato Yano, Tokyo; Takahisa Hayashi, Kyoto, all of (JP)

(73) Assignee: Bio-Polymer Research Co., Ltd., Kawasaki (JP)

( * ) Notice: Subject to any disclaimer, the term of this patent is extended or adjusted under 35 U.S.C. 154(b) by 0 days.

(21) Appl. No.: 09/147,236

(22) PCT Filed: Oct. 9, 1997

(86) PCT No.: PCT/JP97/03633
§ 371 Date: Apr. 8, 1999
§ 102(e) Date: Apr. 8, 1999

(87) PCT Pub. No.: WO98/39455
PCT Pub. Date: Sep. 11, 1998

(30) Foreign Application Priority Data

Mar. 4, 1997 (JP) ................................. 9-063927

(51) Int. Cl.[7] .............................. C12N 15/63; C12N 9/42; C07H 21/04

(52) U.S. Cl. ................ 435/320.1; 435/183; 435/207; 435/224; 435/320.1; 435/209; 536/23.1; 536/23.2; 536/23.74

(58) Field of Search .................................. 435/183, 209, 435/207, 224, 320.1; 536/23.1, 23.2, 23.74

(56) References Cited

U.S. PATENT DOCUMENTS

| 5,268,274 | * | 12/1993 | Ben-Bassat et al. | 435/69.1 |
|---|---|---|---|---|
| 5,580,782 | | 12/1996 | Beppu et al. | 435/252.1 |
| 5,792,630 | | 8/1998 | Tonouchi et al. | 435/101 |

FOREIGN PATENT DOCUMENTS

| 471687 | 6/1992 | (EP) . |
|---|---|---|
| 4-503456 | 6/1982 | (JP) . |
| WO 90/12098 | 6/1992 | (WO) . |

OTHER PUBLICATIONS

Standal et al. A New Gene Required for Cellulose Production and a Gene Encoding Celluloytic Activity in *Acetobacter xylinum* Are Colocalized with the bcs Operon, J. Bacteriol. 176(3): 665–672, Feb. 1994.*

Grabnitz et al. Nucleotide sequence of the *Clostridium thermocellum* bgIB gene encoding thermostable b–glucosidase B: Homology to fungal b–glucosidases, Mol. Gen. Genet. 217: 70–76, May 1989.*

Matsuoka M. et al. "A Synthetic Medium for Bacterial Cellulose Production by Acetobacter Xylinum Subsp. Sucrofermentans" BIOSCI. Biotech. Biochem., vol. 60 No. 4 (1996) pp. 575–579.

Hing C. Wong et al. "Genetic Organization of the Cellulose Synthase Operon in Acetobacter Xylinum", Proc. Natl. Acad. Sci. USA, vol. 87 (Oct. 1990) pp. 8130–8134.

Okamoto T. et al., "Cloning of the Acetobacter Xylinum Cellulase Gene and its Expression in Eschericia Coli and Zymomonas Mobilis", Appl. Microbiol. Biotechnol., vol. 42 (1994) pp. 563–568.

* cited by examiner

*Primary Examiner*—Rebecca E. Prouty
*Assistant Examiner*—Richard Hutson
(74) *Attorney, Agent, or Firm*—Oblon, Spivak, McClelland, Maier & Neustadt, P.C.

(57) ABSTRACT

An object of the present invention is to provide novel genes and gene group involved in cellulose synthesis of microorganisms.

The present invention relates to a gene group encoding cellulase, cellulose synthase complex, β-glucosidase and the like, and to novel β-glucosidase.

16 Claims, 3 Drawing Sheets

SEQUENCE LISTING

<160> NUMBER OF SEQ ID NOS: 12

<210> SEQ ID NO: 1
<211> LENGTH: 16836
<212> TYPE: DNA
<213> ORGANISM: Acetobacter xylinum
<220> FEATURE:
<221> NAME/KEY: CDS
<222> LOCATION: (869)..(1891)
<220> FEATURE:
<221> NAME/KEY: CDS
<222> LOCATION: (3101)..(5368)
<220> FEATURE:
<221> NAME/KEY: CDS
<222> LOCATION: (5373)..(7778)
<220> FEATURE:
<221> NAME/KEY: CDS
<222> LOCATION: (7784)..(11761)
<220> FEATURE:
<221> NAME/KEY: CDS
<222> LOCATION: (11764)..(12231)
<220> FEATURE:
<221> NAME/KEY: CDS
<222> LOCATION: (12448)..(14652)
<220> FEATURE:
<223> OTHER INFORMATION: n at positions 15741 and 15767 may be a, g, t, or c

<400> SEQUENCE: 1

```
ggatccactg gcgcggcgca tcacggcgcg gctggtgctg gggcacccct gaacacaaat      60
gcggggcgtg cgtgattctt tgcttgcatg cccccgcaac atcgcctaga aggcggctac     120
cggccttttg tcccgttcgt ctagaggcct aggacactgc cctctcacgg cggcaacagg     180
ggttcgaatc ccctacggga cgccagccag ttctggctga ataaaagact gactgatgaa     240
aacccgccgc aaggcgggtt tttcgtatgt acttcgtttt tttataaata tctttgacca     300
gaagcctgtc tgcgctatgg caaggcaact ttatttatat taatatataa taaaagcatc     360
ttatatactg cggtctgccc gtctgctaaa aagcattgat ccagatcaat cgcgtctgaa     420
atttaaaaat attttccgtc ttttaatttt gcaaaagatg acaccagtag tgaacggcga     480
tcgtttgcca tattctctt ctttaatttc cttaggaatt atcaacggtt tttacagagg     540
gccatttgcc cctgcgtgac aaaaatgcaa ctttttcttc cctgtagcca gttgtggcgc     600
```

-continued

```
tggtggcggt tcgccgctg gggggagaga cgttatgctc cttttcagta ataaagtctg    660
tcccggaatg gtcgccttcg acttgcagga tggaggagtt tccgattaag gcgtcatggc    720
gtggcagggt attgagggcg catcaggcgt tcggccagac actggcgtgg gttcagactt    780
cttgagggtg tggtggtaga tgctgttgga ttttatgaag ctgcaaaaac atgtatccgg    840
gatggggcgt cgctcctttc tgtccgtc atg gct gtg gct ggc agc ttt ccc       892
                                 Met Ala Val Ala Gly Ser Phe Pro
                                  1               5 atg ctt tcc tcc ggc gct gaa gct gat gat gcc att ggc atc aac ccg      940
Met Leu Ser Ser Gly Ala Glu Ala Asp Asp Ala Ile Gly Ile Asn Pro
     10              15                  20 cag atc gcc cag cag tgg gcc att ttc cgg gac aag tat ttt cat ccc      988
Gln Ile Ala Gln Gln Trp Ala Ile Phe Arg Asp Lys Tyr Phe His Pro
 25              30                  35                      40 aac ggg cgc atc atc gat acg ggc aat agc ggc gaa tcc cac agc gag     1036
Asn Gly Arg Ile Ile Asp Thr Gly Asn Ser Gly Glu Ser His Ser Glu
                 45                  50                  55 ggg cag ggc tac ggc atg ctc ttt tcc gct gcg gcg ggc gac cag gcg     1084
Gly Gln Gly Tyr Gly Met Leu Phe Ser Ala Ala Ala Gly Asp Gln Ala
             60                  65                  70 gcg ttc gag gta atc tgg gtc tgg gcg cgc acc aac ctg cag cac aag     1132
Ala Phe Glu Val Ile Trp Val Trp Ala Arg Thr Asn Leu Gln His Lys
         75                  80                  85 gat gac gcc ctg ttc tcc tgg cgt tac ctt gac ggg cac aaa ccg ccc     1180
Asp Asp Ala Leu Phe Ser Trp Arg Tyr Leu Asp Gly His Lys Pro Pro
     90                  95                  100 gtg gcc gac aag aac aac gca acc gac ggg gac ctg ctc att gcc ctc     1228
Val Ala Asp Lys Asn Asn Ala Thr Asp Gly Asp Leu Leu Ile Ala Leu
105                 110                 115                 120 gcc ctg gct tgg gcc ggc aag cga tgg aag cgc gcc gac tat att cag     1276
Ala Leu Ala Trp Ala Gly Lys Arg Trp Lys Arg Ala Asp Tyr Ile Gln
                125                 130                 135 gac gcc atg aac atc tat ggc gac gtg ctg aaa ctc atg acg aag tcc     1324
Asp Ala Met Asn Ile Tyr Gly Asp Val Leu Lys Leu Met Thr Lys Ser
            140                 145                 150 gtc ggc ccc tac acg gtg ctg ctg ccg ggc gct gtc ggg ttt ctc acc     1372
Val Gly Pro Tyr Thr Val Leu Leu Pro Gly Ala Val Gly Phe Leu Thr
        155                 160                 165 aag gat acg gtc acg ctg aac ctg tcc tat tac gtc atg ccc tcc ctc     1420
Lys Asp Thr Val Thr Leu Asn Leu Ser Tyr Tyr Val Met Pro Ser Leu
    170                 175                 180 atg cag gcc ttt gcg ctc acg ggt gat gcg aag tgg aca aag gtg atg     1468
Met Gln Ala Phe Ala Leu Thr Gly Asp Ala Lys Trp Thr Lys Val Met
185                 190                 195                 200 ggc gac ggg ctg cag atc atc gcc aag gga cga ttc ggt gaa tgg aag     1516
Gly Asp Gly Leu Gln Ile Ile Ala Lys Gly Arg Phe Gly Glu Trp Lys
                205                 210                 215 ctc ccg ccg gac tgg ctg tcg atc aac ctg cat acc aac gcc ttc tcc     1564
Leu Pro Pro Asp Trp Leu Ser Ile Asn Leu His Thr Asn Ala Phe Ser
            220                 225                 230 att gcc aag ggc tgg ccg ccg cgc ttc tcg tat gat gcg att cgc gtg     1612
Ile Ala Lys Gly Trp Pro Pro Arg Phe Ser Tyr Asp Ala Ile Arg Val
        235                 240                 245 ccg ctc tac ttg tct tgg gcg cat atg ctg acc ccg gaa ctg ctg gcg     1660
Pro Leu Tyr Leu Ser Trp Ala His Met Leu Thr Pro Glu Leu Leu Ala
    250                 255                 260 gat ttc agc cgg ttc tgg aac cat tat ggc gca tcc gcc ctg ccg ggc     1708
Asp Phe Ser Arg Phe Trp Asn His Tyr Gly Ala Ser Ala Leu Pro Gly
```

-continued

```
            265                 270                 275                 280
tgg gtt gat ctg acc aac ggc gcg cgt tcg ccc tat aat gcg ccg ccg          1756
Trp Val Asp Leu Thr Asn Gly Ala Arg Ser Pro Tyr Asn Ala Pro Pro
                        285                 290                 295 ggc tat ctg gcg gtg gcg tca tgc acg ggc ctg gcc tcg gcg ggt gaa          1804
Gly Tyr Leu Ala Val Ala Ser Cys Thr Gly Leu Ala Ser Ala Gly Glu
                300                 305                 310 ctg ccc acg ctc gat cat gcg ccc gac tac tat tcg gcg gcg ttg acg          1852
Leu Pro Thr Leu Asp His Ala Pro Asp Tyr Tyr Ser Ala Ala Leu Thr
        315                 320                 325 atg ctg gcc tat atc gcc cgg aac cag gga gat ggg atg tgagcacacc           1901
Met Leu Ala Tyr Ile Ala Arg Asn Gln Gly Asp Gly Met
        330                 335                 340 tgaaaaggaa gcaggaacgc aggtgaatat cgacaaccag caggatgtcg accgtatgct       1961
gacggatggc tacggtatca gcagtgcagg ttttcactac cgccctttca agcagaagcg       2021
cccgcccagg ccagaagtca ggcacgacga gtctggcgca gagcaggccg cagcagccga       2081
gcacgctcct gccgctgaag aagcatcgca gcatttcgtt tcttcctacg atgataccta       2141
ttccaccccg gcagcgcctg aggctgcgcc tgttgaggca gcagaacagc cgcagcacta       2201
cggggaaaca gcctacacgc ctgccgcgca tgatgcctat gccgcacagc cggagccgga       2261
acaggccgcg cccgagcctt atgttgcgca tgacgatacg cccgcagccg aacccgagac       2321
ctatgccgcc acgcacgccg aaaccgtaac ggttccggaa tatgcggccg ccctcagcc        2381
agttgcgacc cccgtgccgc cgcagcccgc gcccgtggcc ccggttgttg ctgccgtggc       2441
gcagccggtc aggcaggagc ggccctcatt gtcgccagtg acgcccccca aacctgcggt       2501
gtcttccttc atggcgcccc gtcctgcccc ggcttttggc tcggcttcag ccacgccccc       2561
catcgcagca gaggactggg ccccgtgcc caaggcccag cagcagcgtg ggcagcgttt        2621
gacagggcca ggcttctttt ttggtgcggg aagtgagcgg gcgcccgcag caaggctgtt       2681
ccagtcggca ccggtgtccc ggcctgtttc aaaacctgtt tccaaggtga ccacaatgac       2741
caaagttgac aagagttccc cgaatgacag tcaggcaggc cgccctgcac cgaccgacaa       2801
ttctccgacc ctgaccgaag tgttcatgac ccttggcggt cgggccacgg atcggctggt       2861
gcccaagccc agcctgcgtg atgccctgtt gcgcaagcgt gaaggcacga acggcgaatc       2921
ctgacaccgt gccgggagca gtctgctccc ggcctgccaa aggaaagaag ggggaaggtt      2981
ttccccatcc cgcacaagcg gcgggccgaa aggcgacatg acggaccgaa tcgtctctgac    3041
ggttttcttt tgaatatatc tacctgtttt atcagtattt attatcggac gagctattg       3100 atg tca gag gtt cag tcg cca gta ccc acg gag agt agg cta ggc cgc          3148
Met Ser Glu Val Gln Ser Pro Val Pro Thr Glu Ser Arg Leu Gly Arg
                        345                 350                 355 atc tcc aac aag ata ctg tca ctg cgt ggg gcc agc tat ata gtt gga          3196
Ile Ser Asn Lys Ile Leu Ser Leu Arg Gly Ala Ser Tyr Ile Val Gly
                360                 365                 370 gcg ctg ggg ctt tgt gca ctt att gcc gcg acc acg gtt acg ctg aac          3244
Ala Leu Gly Leu Cys Ala Leu Ile Ala Ala Thr Thr Val Thr Leu Asn
        375                 380                 385 aat aat gag cag cta att gtg gca gct gta tgt gtt gtc atc ttt ttt          3292
Asn Asn Glu Gln Leu Ile Val Ala Ala Val Cys Val Val Ile Phe Phe
390                 395                 400                 405 gtt gtc ggg cgt ggc aag agc cgg cgc acc cag att ttt ctc gag gtg          3340
Val Val Gly Arg Gly Lys Ser Arg Arg Thr Gln Ile Phe Leu Glu Val
                        410                 415                 420 ctc tcc gcg ctg gtt tcc ctg cgt tac ctg aca tgg cgc ctg acc gaa          3388
```

```
                          -continued

Leu Ser Ala Leu Val Ser Leu Arg Tyr Leu Thr Trp Arg Leu Thr Glu
            425                 430                 435 acg ctc gac ttc aat aca tgg att cag ggc ata ctg ggc gta atc ctg      3436
Thr Leu Asp Phe Asn Thr Trp Ile Gln Gly Ile Leu Gly Val Ile Leu
            440                 445                 450 ctc atg gcc gag ctg tat gcc ctg tac atg ctg ttt ctc agc tat ttc      3484
Leu Met Ala Glu Leu Tyr Ala Leu Tyr Met Leu Phe Leu Ser Tyr Phe
            455                 460                 465 cag aca atc cag ccg ctt cat cgt gcg ccg ctg ccc ctg cct gac aat      3532
Gln Thr Ile Gln Pro Leu His Arg Ala Pro Leu Pro Leu Pro Asp Asn
470                 475                 480                 485 gtt gac gac tgg ccg act gtc gat atc ttc atc ccg acc tat gat gag      3580
Val Asp Asp Trp Pro Thr Val Asp Ile Phe Ile Pro Thr Tyr Asp Glu
                490                 495                 500 cag ctg agc atc gtg cgc ctg acc gtg ctg ggc gcg ctc ggc atc gac      3628
Gln Leu Ser Ile Val Arg Leu Thr Val Leu Gly Ala Leu Gly Ile Asp
                505                 510                 515 tgg ccg ccc gat aaa gtg aat gtc tat atc ctt gat gac ggt gtg cgg      3676
Trp Pro Pro Asp Lys Val Asn Val Tyr Ile Leu Asp Asp Gly Val Arg
                520                 525                 530 ccc gaa ttc gag cag ttc gcc aag gat tgc ggc gcc ctg tat atc ggg      3724
Pro Glu Phe Glu Gln Phe Ala Lys Asp Cys Gly Ala Leu Tyr Ile Gly
            535                 540                 545 cgt gtc gac gtc gac agc gcg cac gcc aag gcg ggt aac ctc aac cac      3772
Arg Val Asp Val Asp Ser Ala His Ala Lys Ala Gly Asn Leu Asn His
550                 555                 560                 565 gcc att aag cgg act tcc ggc gat tac atc ctc atc ctg gat tgt gac      3820
Ala Ile Lys Arg Thr Ser Gly Asp Tyr Ile Leu Ile Leu Asp Cys Asp
                570                 575                 580 cat att ccg aca cgc gcg ttc ctg cag atc gcc atg ggg tgg atg gtc      3868
His Ile Pro Thr Arg Ala Phe Leu Gln Ile Ala Met Gly Trp Met Val
                585                 590                 595 gct gac cgc aag atc gcc ctg atg cag acg ccg cat cac ttc tac tct      3916
Ala Asp Arg Lys Ile Ala Leu Met Gln Thr Pro His His Phe Tyr Ser
            600                 605                 610 ccc gat ccg ttc cag cgt aac ctg gcc gtg ggc tac cgc acc ccg ccg      3964
Pro Asp Pro Phe Gln Arg Asn Leu Ala Val Gly Tyr Arg Thr Pro Pro
            615                 620                 625 gaa ggc aac ctg ttc tac ggc gtc atc cag gat ggc aac gac ttc tgg      4012
Glu Gly Asn Leu Phe Tyr Gly Val Ile Gln Asp Gly Asn Asp Phe Trp
630                 635                 640                 645 gat gcc acc ttc ttc tgc ggc tca tgc gcc atc ctg cgg cgt gag gcc      4060
Asp Ala Thr Phe Phe Cys Gly Ser Cys Ala Ile Leu Arg Arg Glu Ala
                650                 655                 660 att gaa tcg atc ggc ggc ttt gcg gtt gaa acc gtg acg gaa gat gcc      4108
Ile Glu Ser Ile Gly Gly Phe Ala Val Glu Thr Val Thr Glu Asp Ala
                665                 670                 675 cat acc gcc ctg cgc atg cag cgc cgc ggc tgg tcc acc gct tac ctg      4156
His Thr Ala Leu Arg Met Gln Arg Arg Gly Trp Ser Thr Ala Tyr Leu
            680                 685                 690 cgc att ccc gtt gcc agt ggt ctg gcc acc gag cga ctg acc acc cat      4204
Arg Ile Pro Val Ala Ser Gly Leu Ala Thr Glu Arg Leu Thr Thr His
            695                 700                 705 atc ggc cag cgc atg cgc tgg gcg cgc ggc atg atc cag atc ttc cgc      4252
Ile Gly Gln Arg Met Arg Trp Ala Arg Gly Met Ile Gln Ile Phe Arg
710                 715                 720                 725 gtg gat aac ccg atg ctc ggg cgc ggc ctg aag ttg ggc cag cgg ctt      4300
Val Asp Asn Pro Met Leu Gly Arg Gly Leu Lys Leu Gly Gln Arg Leu
                730                 735                 740
```

```
tgc tat ctt tcg gcc atg acg tcg ttc ttc ttc gcc att ccg cgc gtt      4348
Cys Tyr Leu Ser Ala Met Thr Ser Phe Phe Phe Ala Ile Pro Arg Val
        745                 750                 755 atc ttc ctt gcc tcg ccg ctg gcg ttc ctg ttt gcg ggc cag aac atc      4396
Ile Phe Leu Ala Ser Pro Leu Ala Phe Leu Phe Ala Gly Gln Asn Ile
760                 765                 770 atc gcc gcc gcg cca ctg gcc gtg gcg gcc tat gcc ctc ccg cac atg      4444
Ile Ala Ala Ala Pro Leu Ala Val Ala Ala Tyr Ala Leu Pro His Met
    775                 780                 785 ttc cac tcc att gca acc gcc gcc aag gtg aac aag ggc tgg cgc tat      4492
Phe His Ser Ile Ala Thr Ala Ala Lys Val Asn Lys Gly Trp Arg Tyr
790                 795                 800                 805 tcg ttc tgg agt gag gtg tac gaa acc acc atg gcg ctg ttc ctg gtg      4540
Ser Phe Trp Ser Glu Val Tyr Glu Thr Thr Met Ala Leu Phe Leu Val
            810                 815                 820 cgc gtg acc atc gtc acc ctg ctg ttc ccc tcc aag ggc aaa ttc aac      4588
Arg Val Thr Ile Val Thr Leu Leu Phe Pro Ser Lys Gly Lys Phe Asn
                825                 830                 835 gtg acg gaa aag ggc ggc gtg ctt gag gag gaa gag ttc gat ctt ggg      4636
Val Thr Glu Lys Gly Gly Val Leu Glu Glu Glu Glu Phe Asp Leu Gly
        840                 845                 850 gcg acc tac ccc aac atc att ttc gcc acc atc atg atg ggt ggc ctg      4684
Ala Thr Tyr Pro Asn Ile Ile Phe Ala Thr Ile Met Met Gly Gly Leu
855                 860                 865 ctg atc ggt ctg ttc gag ttg atc gtg cgt ttc aat cag ctc gat gtc      4732
Leu Ile Gly Leu Phe Glu Leu Ile Val Arg Phe Asn Gln Leu Asp Val
870                 875                 880                 885 att gcc agg aac gct tat ctc ctg aac tgc gcc tgg gcg ctg atc agt      4780
Ile Ala Arg Asn Ala Tyr Leu Leu Asn Cys Ala Trp Ala Leu Ile Ser
            890                 895                 900 ctc atc atc ctt ttc gct gcc att gcc gtg ggg cgc gag acc aag cag      4828
Leu Ile Ile Leu Phe Ala Ala Ile Ala Val Gly Arg Glu Thr Lys Gln
                905                 910                 915 gtc cgt tac aac cat cgt gtc gaa gcg cat atc ccg gta acg gtt tac      4876
Val Arg Tyr Asn His Arg Val Glu Ala His Ile Pro Val Thr Val Tyr
        920                 925                 930 gat gcg cct gcc gaa ggg cag ccc cat acc tat tat aat gcg acg cac      4924
Asp Ala Pro Ala Glu Gly Gln Pro His Thr Tyr Tyr Asn Ala Thr His
935                 940                 945 ggc atg acc cag gat gtt tcc atg ggt ggt gtt gcc gtg cac atc ccc      4972
Gly Met Thr Gln Asp Val Ser Met Gly Gly Val Ala Val His Ile Pro
950                 955                 960                 965 ttg ccc gat gtc acc acg ggg cct gtc aag aaa cgt atc cat gcc gtg      5020
Leu Pro Asp Val Thr Thr Gly Pro Val Lys Lys Arg Ile His Ala Val
            970                 975                 980 ctt gat ggc gag gaa atc cat att ccc gcc acc atg ctg cgc tgc acg      5068
Leu Asp Gly Glu Glu Ile His Ile Pro Ala Thr Met Leu Arg Cys Thr
                985                 990                 995 aat ggc aag gcc gtg ttc aca tgg gac aat aat gac ctt gat acg gaa      5116
Asn Gly Lys Ala Val Phe Thr Trp Asp Asn Asn Asp Leu Asp Thr Glu
        1000                1005                1010 cgc gat att gtc cgc ttc gtg ttc ggg cgg gct gat gcc tgg ctg caa      5164
Arg Asp Ile Val Arg Phe Val Phe Gly Arg Ala Asp Ala Trp Leu Gln
1015                1020                1025 tgg aac aat tat gag gat gac aga ccg cta cgc agc ctg tgg agc ctg      5212
Trp Asn Asn Tyr Glu Asp Asp Arg Pro Leu Arg Ser Leu Trp Ser Leu
1030                1035                1040                1045 ctg ctc agc att aag gcg ctg ttc cgc aaa aaa ggc aaa ata atg gcc      5260
Leu Leu Ser Ile Lys Ala Leu Phe Arg Lys Lys Gly Lys Ile Met Ala
            1050                1055                1060
```

```
aat agt cgt cca aaa aag aaa cca ctt gca cta ccg gtt gag cgc agg    5308
Asn Ser Arg Pro Lys Lys Lys Pro Leu Ala Leu Pro Val Glu Arg Arg
            1065                1070                1075 gag ccc aca acc atc cac agt gga cag act caa gaa gga aag atc agc    5356
Glu Pro Thr Thr Ile His Ser Gly Gln Thr Gln Glu Gly Lys Ile Ser
        1080                1085                1090 cgt gcg gcc tcg tgat atg aaa atg gtg tcc ctg atc gcg ctg ctg gtc   5405
Arg Ala Ala Ser      Met Lys Met Val Ser Leu Ile Ala Leu Leu Val
    1095                 1100                1105 ttt gca acg ggg gca cag gct gcg cct gtt gct tcc aag gcg cca gct    5453
Phe Ala Thr Gly Ala Gln Ala Ala Pro Val Ala Ser Lys Ala Pro Ala
    1110                1115                1120 ccg cag ccc gca ggt tca gac ctg cca cct ctc cct gcc gca ccg ccg    5501
Pro Gln Pro Ala Gly Ser Asp Leu Pro Pro Leu Pro Ala Ala Pro Pro
1125                1130                1135                1140 cag gct gct ccg ccc gca gcc gcg agt gcc gcc ccg ccc gcc aca acc    5549
Gln Ala Ala Pro Pro Ala Ala Ala Ser Ala Ala Pro Pro Ala Thr Thr
                1145                1150                1155 ccg gcg gcg gat gcc tca gca gcc agc gcg gct gat gcg gtt gtg gac    5597
Pro Ala Ala Asp Ala Ser Ala Ala Ser Ala Ala Asp Ala Val Val Asp
            1160                1165                1170 aat gcc gag aac gcc atc gcc ggg tct gac gtg gcg acg gtg cat aca    5645
Asn Ala Glu Asn Ala Ile Ala Gly Ser Asp Val Ala Thr Val His Thr
        1175                1180                1185 tat tcc ctc agg gaa ctt ggt gcg cag agt gcc ctc aaa atg cag ggc    5693
Tyr Ser Leu Arg Glu Leu Gly Ala Gln Ser Ala Leu Lys Met Gln Gly
    1190                1195                1200 gct gct acg ctg cag ggc ctg cag ttc ggt att ccg gcc gac cag ctc    5741
Ala Ala Thr Leu Gln Gly Leu Gln Phe Gly Ile Pro Ala Asp Gln Leu
1205                1210                1215                1220 gtg act tcg gcg cgg ctt gtc gtg tcg ggt gcg atg tcg ccc agc ctc    5789
Val Thr Ser Ala Arg Leu Val Val Ser Gly Ala Met Ser Pro Ser Leu
                1225                1230                1235 cag cct gac acc agc gcg gtc acg atc acg ctg aac gaa cag ttc atc    5837
Gln Pro Asp Thr Ser Ala Val Thr Ile Thr Leu Asn Glu Gln Phe Ile
            1240                1245                1250 ggc acg ctg cgg cct gac ccc aca cac cct aca ttt ggg ccg ctt tcg    5885
Gly Thr Leu Arg Pro Asp Pro Thr His Pro Thr Phe Gly Pro Leu Ser
        1255                1260                1265 ttt gat atc aac ccc atc ttc ttc atc agt ggc aac cgg ctg aat ttc    5933
Phe Asp Ile Asn Pro Ile Phe Phe Ile Ser Gly Asn Arg Leu Asn Phe
    1270                1275                1280 agc ttc gct tca agc tcg aag ggc tgc acg gac ccc agc aac ggg ttg    5981
Ser Phe Ala Ser Ser Ser Lys Gly Cys Thr Asp Pro Ser Asn Gly Leu
1285                1290                1295                1300 ttc tgg gcc agc gtg tcc gaa cat tcc gag ctg cag atc acc acc atc    6029
Phe Trp Ala Ser Val Ser Glu His Ser Glu Leu Gln Ile Thr Thr Ile
                1305                1310                1315 ccg ctt ccc ccg cat cgc cag ctg tcg cgt ctg ccc cag ccg ttc ttc    6077
Pro Leu Pro Pro His Arg Gln Leu Ser Arg Leu Pro Gln Pro Phe Phe
            1320                1325                1330 gac aag aac gta aag cag aag atc gtc att ccg ttc gtt ctc gca cag    6125
Asp Lys Asn Val Lys Gln Lys Ile Val Ile Pro Phe Val Leu Ala Gln
        1335                1340                1345 aca ttt gat ccc gaa gtg ctg aag gcg acg ggc atc ctg gca tcg tgg    6173
Thr Phe Asp Pro Glu Val Leu Lys Ala Thr Gly Ile Leu Ala Ser Trp
    1350                1355                1360 ttc ggc cag cag acc gat tac cgt ggc gtc acc ttc ccg gtc ttc tcc    6221
Phe Gly Gln Gln Thr Asp Tyr Arg Gly Val Thr Phe Pro Val Phe Ser
```

-continued

```
      1365                1370                1375                1380
acc att ccg caa acg ggc aac gcc gtt gtt gtc ggc gtg gct gac gag       6269
Thr Ile Pro Gln Thr Gly Asn Ala Val Val Val Gly Val Ala Asp Glu
            1385                1390                1395 ctg cct tcc gcc ctc ggg cgc cag gcg gtc agt ggc ccc acg ctt atg       6317
Leu Pro Ser Ala Leu Gly Arg Gln Ala Val Ser Gly Pro Thr Leu Met
        1400                1405                1410 gaa gtg gcc aat cca tcc gac ccc aac ggc acg atc ctg ctc gta acc       6365
Glu Val Ala Asn Pro Ser Asp Pro Asn Gly Thr Ile Leu Leu Val Thr
    1415                1420                1425 ggg cgc gac cgt gat gaa gtc atc acc gcg agc aag ggc atc ggt ttt       6413
Gly Arg Asp Arg Asp Glu Val Ile Thr Ala Ser Lys Gly Ile Gly Phe
 1430                1435                1440 ggt tcg agc acc ctg ccg aca gcc aac cgc atg gac gtg gcg ccg atc       6461
Gly Ser Ser Thr Leu Pro Thr Ala Asn Arg Met Asp Val Ala Pro Ile
1445                1450                1455                1460 gag gtc ggg gcc cgc gtg gcg aat gac gcg ccc tcc ttc att ccg acc       6509
Glu Val Gly Ala Arg Val Ala Asn Asp Ala Pro Ser Phe Ile Pro Thr
                1465                1470                1475 aac cgc ccg gtc cgc ctg ggc gaa ctg gtg cca gac agc gcc ctg cag       6557
Asn Arg Pro Val Arg Leu Gly Glu Leu Val Pro Asp Ser Ala Leu Gln
            1480                1485                1490 gct gaa ggt tac gcc cct ggc gcg ctg gcg gtg cca ttc cgt gtc tcg       6605
Ala Glu Gly Tyr Ala Pro Gly Ala Leu Ala Val Pro Phe Arg Val Ser
        1495                1500                1505 cct gac ctg tat acg tgg cgc gat cgg ccg aac aag ctg aac gtc cgt       6653
Pro Asp Leu Tyr Thr Trp Arg Asp Arg Pro Asn Lys Leu Asn Val Arg
    1510                1515                1520 ttc cgc gcg ccg ccg ggg ccg atc gtg gat gtg tcg cgc tcg tcg ctc       6701
Phe Arg Ala Pro Pro Gly Pro Ile Val Asp Val Ser Arg Ser Ser Leu
1525                1530                1535                1540 aat gta ggc atc aac gat acc tat ctc gag gcc tat ccg ctg cgt gag       6749
Asn Val Gly Ile Asn Asp Thr Tyr Leu Glu Ala Tyr Pro Leu Arg Glu
                1545                1550                1555 ccg gat tca ccg ctg gac cag ctc ctg cat ggg gtg ggc ctt ggc cat       6797
Pro Asp Ser Pro Leu Asp Gln Leu Leu His Gly Val Gly Leu Gly His
            1560                1565                1570 cgt aat aat gac agc gtg cag cag cac acc atg ccc atc ccg acc tac       6845
Arg Asn Asn Asp Ser Val Gln Gln His Thr Met Pro Ile Pro Thr Tyr
        1575                1580                1585 cgg gtc ttt ggc cag aac cag ctg ctg ttc tat ttc gag atg gcg gcg       6893
Arg Val Phe Gly Gln Asn Gln Leu Leu Phe Tyr Phe Glu Met Ala Ala
    1590                1595                1600 atg gtc gag ccg ggc tgc aaa ccc ggc ccg agc acg ttc cat atg ggc       6941
Met Val Glu Pro Gly Cys Lys Pro Gly Pro Ser Thr Phe His Met Gly
1605                1610                1615                1620 att gat ccc aat tcg acg atc gat ctg tcc aac tcc tat cac atc acc       6989
Ile Asp Pro Asn Ser Thr Ile Asp Leu Ser Asn Ser Tyr His Ile Thr
                1625                1630                1635 cag atg ccc aac ctc gcc ttc atg gcc agt gcg ggc ttt ccg ttc acc       7037
Gln Met Pro Asn Leu Ala Phe Met Ala Ser Ala Gly Phe Pro Phe Thr
            1640                1645                1650 acc tat gcc gac ctg tcg cgc tcg gcc gtg gtg ctg ccc gaa cac ccc       7085
Thr Tyr Ala Asp Leu Ser Arg Ser Ala Val Val Leu Pro Glu His Pro
        1655                1660                1665 aat ggc atg att gtc agc gcc tat ctc gac ctc atg ggc ttc atg ggg       7133
Asn Gly Met Ile Val Ser Ala Tyr Leu Asp Leu Met Gly Phe Met Gly
    1670                1675                1680 gcg acg aca tgg tat ccg gtg tct ggc gtt gat gtg gtc tcc agc gac       7181
```

-continued

```
Ala Thr Thr Trp Tyr Pro Val Ser Gly Val Asp Val Ser Ser Asp
1685                1690                1695                1700 cat gtg aat gac gtg gcg gac cgg aac ctg att gtc ctg tcc acg ctg         7229
His Val Asn Asp Val Ala Asp Arg Asn Leu Ile Val Leu Ser Thr Leu
           1705                1710                1715 gcc aat agc ggt gat gtt tcg cag ctg ctg agc aat tcg gcc tat cag         7277
Ala Asn Ser Gly Asp Val Ser Gln Leu Leu Ser Asn Ser Ala Tyr Gln
     1720                1725                1730 att tcc gat ggg cgg ctg cac atg gcc ctg cgt tcg acg ctg agc ggc         7325
Ile Ser Asp Gly Arg Leu His Met Ala Leu Arg Ser Thr Leu Ser Gly
 1735                1740                1745 gtg tgg aac ctt ttc cag gat ccc atg tcg gcc atc aac agc acg gcc         7373
Val Trp Asn Leu Phe Gln Asp Pro Met Ser Ala Ile Asn Ser Thr Ala
   1750                1755                1760 ccg acc gat gtc gag agc acg ctg acc ggt ggc gtg gcc gcg atg gtc         7421
Pro Thr Asp Val Glu Ser Thr Leu Thr Gly Gly Val Ala Ala Met Val
1765                1770                1775                1780 gag gcg gaa tcg ccg ctg gca tcg ggt cgg acc gtt ctc gcg ctg ctt         7469
Glu Ala Glu Ser Pro Leu Ala Ser Gly Arg Thr Val Leu Ala Leu Leu
           1785                1790                1795 tcg ggt gac ggg cag ggg ctc aac aac ctt gtg cag atc ctg gcg cag         7517
Ser Gly Asp Gly Gln Gly Leu Asn Asn Leu Val Gln Ile Leu Ala Gln
     1800                1805                1810 cgg aaa aac cag gcc aag atc cag ggt gat ctg gtg ctg gca cat ggg         7565
Arg Lys Asn Gln Ala Lys Ile Gln Gly Asp Leu Val Leu Ala His Gly
 1815                1820                1825 gat gac ctg acc tcc tac cgc agc tcg ccg ctg tat acg gtt ggc acc         7613
Asp Asp Leu Thr Ser Tyr Arg Ser Ser Pro Leu Tyr Thr Val Gly Thr
   1830                1835                1840 gtg ccg ctg tgg ctc aag cct gac tgg tat atg cac aac cat ccc agc         7661
Val Pro Leu Trp Leu Lys Pro Asp Trp Tyr Met His Asn His Pro Ser
1845                1850                1855                1860 cgc gtg gtc gtg gtt ggc ctg ttc ggt tgc ctt ctg gtg gtg gct gtc         7709
Arg Val Val Val Val Gly Leu Phe Gly Cys Leu Leu Val Val Ala Val
           1865                1870                1875 ctg atg cgc gcc ctg acc aag cat gct ctg cgc cgc cgt cgg gag ttg         7757
Leu Met Arg Ala Leu Thr Lys His Ala Leu Arg Arg Arg Arg Glu Leu
     1880                1885                1890 cag gaa gaa agg cag aga acg tgatc atg aac agg cga tac gcc ctt tcg      7807
Gln Glu Glu Arg Gln Arg Thr       Met Asn Arg Arg Tyr Ala Leu Ser
 1895                1900                1905 ctt tct ggt gcc ctg ctg gcc agc agt tgc atg acg gtg ctg gtg gcg         7855
Leu Ser Gly Ala Leu Leu Ala Ser Ser Cys Met Thr Val Leu Val Ala
   1910                1915                1920 gtt cct gtt gcg cgg gcg cag cag gct tcc act gcc gtg act tcc aca         7903
Val Pro Val Ala Arg Ala Gln Gln Ala Ser Thr Ala Val Thr Ser Thr
1925                1930                1935 gcc gcg agt ccg gct gcg gcc cca cgg cag atc ctg ttg cag cag gca         7951
Ala Ala Ser Pro Ala Ala Ala Pro Arg Gln Ile Leu Leu Gln Gln Ala
1940                1945                1950                1955 cgc ttc tgg ctt cag cag cag caa tat gac aat gcc cgc cag gcc ctg         7999
Arg Phe Trp Leu Gln Gln Gln Gln Tyr Asp Asn Ala Arg Gln Ala Leu
           1960                1965                1970 cag aat gcg cag cgc atc gcc ccc gat gcc cct gac gtg ctg gaa gtg         8047
Gln Asn Ala Gln Arg Ile Ala Pro Asp Ala Pro Asp Val Leu Glu Val
     1975                1980                1985 gag ggt gaa tac cag gcg gcc gtt ggc aac cgc gaa gcc gct gcc gat         8095
Glu Gly Glu Tyr Gln Ala Ala Val Gly Asn Arg Glu Ala Ala Ala Asp
 1990                1995                2000
```

```
acc ctg cgc cac ctg cag cag gtg gcc ccg gcc agc acg gcg gtc agc    8143
Thr Leu Arg His Leu Gln Gln Val Ala Pro Ala Ser Thr Ala Val Ser
    2005                2010                2015 aac ctg agc gat ctg ctc agc gag cgg gcc att tcc caa agc gac ctg    8191
Asn Leu Ser Asp Leu Leu Ser Glu Arg Ala Ile Ser Gln Ser Asp Leu
2020                2025                2030                2035 tca cag atc cgt tcg ctg gcg ggt tcg ggc cag aac gcg cag gcg gtg    8239
Ser Gln Ile Arg Ser Leu Ala Gly Ser Gly Gln Asn Ala Gln Ala Val
            2040                2045                2050 gcg ggg tac cag aag ctg ttc cac ggt ggc aag ccg ccc cgt tcg ctt    8287
Ala Gly Tyr Gln Lys Leu Phe His Gly Gly Lys Pro Pro Arg Ser Leu
                2055                2060                2065 gcg gtg gaa tac tac cag acc atg gcg ggc gtg ccg acc cag tgg gac    8335
Ala Val Glu Tyr Tyr Gln Thr Met Ala Gly Val Pro Thr Gln Trp Asp
        2070                2075                2080 cag gcg cgc gcg ggg ctg gcc ggg atc gtt gcg tcc aac ccg cag aat    8383
Gln Ala Arg Ala Gly Leu Ala Gly Ile Val Ala Ser Asn Pro Gln Asn
    2085                2090                2095 tac cgc gcc cag ctc gcc ttt gcc cag gcc ctg acc tat aat acc tcg    8431
Tyr Arg Ala Gln Leu Ala Phe Ala Gln Ala Leu Thr Tyr Asn Thr Ser
2100                2105                2110                2115 acc cgc atg gaa ggc ctg acc cgg ctc aag gat ctg caa tcc ttc cag    8479
Thr Arg Met Glu Gly Leu Thr Arg Leu Lys Asp Leu Gln Ser Phe Gln
            2120                2125                2130 agt cag gcc ccg gtc gaa gct gcc gcc gcg acg cag tcc tat cgc cag    8527
Ser Gln Ala Pro Val Glu Ala Ala Ala Ala Thr Gln Ser Tyr Arg Gln
                2135                2140                2145 acc ctg agc tgg ctg ccg gtc aat ccc gat acg cag ccc ctc atg gag    8575
Thr Leu Ser Trp Leu Pro Val Asn Pro Asp Thr Gln Pro Leu Met Glu
        2150                2155                2160 cag tgg ctt tcc gcc cac ccc aat gat gcc gcg ctg cgc gaa cac atg    8623
Gln Trp Leu Ser Ala His Pro Asn Asp Ala Ala Leu Arg Glu His Met
    2165                2170                2175 ctt cac ccc ccc ggc ggc ccg ccg gac aaa gcg ggg ctt gcg cgg cag    8671
Leu His Pro Pro Gly Gly Pro Pro Asp Lys Ala Gly Leu Ala Arg Gln
2180                2185                2190                2195 gcc ggt tac cag cag ctc aac gcg ggc cgt ctt tcc gct gcc gaa cag    8719
Ala Gly Tyr Gln Gln Leu Asn Ala Gly Arg Leu Ser Ala Ala Glu Gln
            2200                2205                2210 tcc ttc cag tcg gcg ttg cag atc aac tcc cat gat gct gat tca ctg    8767
Ser Phe Gln Ser Ala Leu Gln Ile Asn Ser His Asp Ala Asp Ser Leu
                2215                2220                2225 ggt ggc atg ggc ctc gtg agc atg cgg cag ggc gat acc gcc gag gcg    8815
Gly Gly Met Gly Leu Val Ser Met Arg Gln Gly Asp Thr Ala Glu Ala
        2230                2235                2240 cac ccc tat ttt gaa gag gcg atg gcc gcc gac ccc aag act gcc gat    8863
His Pro Tyr Phe Glu Glu Ala Met Ala Ala Asp Pro Lys Thr Ala Asp
    2245                2250                2255 cgc tgg cgc ccg gcg ctt gcg ggc atg gcg gtc agc ggg gac tat gcc    8911
Arg Trp Arg Pro Ala Leu Ala Gly Met Ala Val Ser Gly Asp Tyr Ala
2260                2265                2270                2275 gcc gtt cgc cag ttg att gcc gcc cat cag tat acc gag gcc aag cag    8959
Ala Val Arg Gln Leu Ile Ala Ala His Gln Tyr Thr Glu Ala Lys Gln
            2280                2285                2290 aag ctt gcc acg ctg gcc cgc cag ccc ggg cag tac acc ggc gcg acc    9007
Lys Leu Ala Thr Leu Ala Arg Gln Pro Gly Gln Tyr Thr Gly Ala Thr
                2295                2300                2305 ctc atg ctg gcc gac ctg cag cgc tcg acc ggg cag gtt gcc gcc gcc    9055
Leu Met Leu Ala Asp Leu Gln Arg Ser Thr Gly Gln Val Ala Ala Ala
        2310                2315                2320
```

```
gag cag gaa tat cgt ggc atc ctg tcg cgt gag ccc aat aac cag ctg      9103
Glu Gln Glu Tyr Arg Gly Ile Leu Ser Arg Glu Pro Asn Asn Gln Leu
        2325                2330                2335 gcc ctt atg ggg ctg gcg cgg gtg gac atg gcg cag ggc aac acg gcg      9151
Ala Leu Met Gly Leu Ala Arg Val Asp Met Ala Gln Gly Asn Thr Ala
2340                2345                2350                2355 gaa gca cgc cag ctc ctg tcg cgt gtg agc ccg caa tat gcc agc cag      9199
Glu Ala Arg Gln Leu Leu Ser Arg Val Ser Pro Gln Tyr Ala Ser Gln
            2360                2365                2370 gtc ggg gaa atc gag gtt tcc ggc ctt atg gcg gca gcg tcg cag aca      9247
Val Gly Glu Ile Glu Val Ser Gly Leu Met Ala Ala Ala Ser Gln Thr
            2375                2380                2385 tcg gat tca gcg cgc aag gtt tcc atc ctg cgc gaa gcg atg gcc cag      9295
Ser Asp Ser Ala Arg Lys Val Ser Ile Leu Arg Glu Ala Met Ala Gln
        2390                2395                2400 gcc ccg cgt gac ccg tgg gtg cgc atc aac ctt gcc aat gcg ctg cag      9343
Ala Pro Arg Asp Pro Trp Val Arg Ile Asn Leu Ala Asn Ala Leu Gln
2405                2410                2415 cag cag ggc gat gtg gct gaa gcc ggg cgc gtg atg cag ccc atc ctg      9391
Gln Gln Gly Asp Val Ala Glu Ala Gly Arg Val Met Gln Pro Ile Leu
2420                2425                2430                2435 gcc aat cct gtc acc gcg cag gac cgc cag gcc ggt atc ctg tat acc      9439
Ala Asn Pro Val Thr Ala Gln Asp Arg Gln Ala Gly Ile Leu Tyr Thr
            2440                2445                2450 tat ggc agt ggc aat gat gcg atg acc cgc cag ctt ctg gcc ggt ctg      9487
Tyr Gly Ser Gly Asn Asp Ala Met Thr Arg Gln Leu Leu Ala Gly Leu
            2455                2460                2465 tcg ccc gcg gat tat tcc ccc gcg atc cgt tcc att gcc gag gaa atg      9535
Ser Pro Ala Asp Tyr Ser Pro Ala Ile Arg Ser Ile Ala Glu Glu Met
        2470                2475                2480 gaa atc aag cag gac ctg gcc agc cgc ctg tcg atg gta tcc aac ccg      9583
Glu Ile Lys Gln Asp Leu Ala Ser Arg Leu Ser Met Val Ser Asn Pro
2485                2490                2495 gtg ccg ctg atc cgc gag gcc ctt tcc cag cct gat ccg acc ggc gcg      9631
Val Pro Leu Ile Arg Glu Ala Leu Ser Gln Pro Asp Pro Thr Gly Ala
2500                2505                2510                2515 cgt ggc gtg gcg gtg gcc gac ctg ttc cgc cag cgt ggc gac atg gtg      9679
Arg Gly Val Ala Val Ala Asp Leu Phe Arg Gln Arg Gly Asp Met Val
            2520                2525                2530 cat gcg cgc atg gcg ctg cgt atc gcc tcg acg cgc acc atc gac ctt      9727
His Ala Arg Met Ala Leu Arg Ile Ala Ser Thr Arg Thr Ile Asp Leu
            2535                2540                2545 tcg ccc gac cag cgc ctg tcc tac gcc acc gaa tac atg aag atc agc      9775
Ser Pro Asp Gln Arg Leu Ser Tyr Ala Thr Glu Tyr Met Lys Ile Ser
        2550                2555                2560 aac ccg gtg gca gcc gca cgc ctg ctg gcc ccg ctg ggg gat ggc acg      9823
Asn Pro Val Ala Ala Ala Arg Leu Leu Ala Pro Leu Gly Asp Gly Thr
2565                2570                2575 ggt tcg ggc gcg ggc aat gcg ctg ctg ccc gag cag atg cag aca ttg      9871
Gly Ser Gly Ala Gly Asn Ala Leu Leu Pro Glu Gln Met Gln Thr Leu
2580                2585                2590                2595 cag caa ctg cgc atg ggc atc tcg gtg gcg cag tcg gat ctg ctc aac      9919
Gln Gln Leu Arg Met Gly Ile Ser Val Ala Gln Ser Asp Leu Leu Asn
            2600                2605                2610 cag cgt ggc gat cag gcg cag gcc tac gat cat ctg gcg ccc gcc ctg      9967
Gln Arg Gly Asp Gln Ala Gln Ala Tyr Asp His Leu Ala Pro Ala Leu
            2615                2620                2625 cag gcc gac ccg gag gcg aca tcg ccc aag ctg gcg ctc gcg cgg ctg     10015
Gln Ala Asp Pro Glu Ala Thr Ser Pro Lys Leu Ala Leu Ala Arg Leu
```

-continued

```
            2630                2635                2640
tat aac ggc cac ggc aag ccg ggc aag gcg ctc gag atc gac ctt gcg     10063
Tyr Asn Gly His Gly Lys Pro Gly Lys Ala Leu Glu Ile Asp Leu Ala
        2645                2650                2655 gtg ctg cgc cac aac ccg cag gat ctt gat gcg cgg cag gcg gcg gtg     10111
Val Leu Arg His Asn Pro Gln Asp Leu Asp Ala Arg Gln Ala Ala Val
2660                2665                2670                2675 cag gcg gcg gtc aac agc aac cac aac agt ctt gcc acc cgt ctc gcg     10159
Gln Ala Ala Val Asn Ser Asn His Asn Ser Leu Ala Thr Arg Leu Ala
            2680                2685                2690 atg gat ggc gtg cag gaa agc ccg atg gat gcc cgc gcc tgg ctg gcc     10207
Met Asp Gly Val Gln Glu Ser Pro Met Asp Ala Arg Ala Trp Leu Ala
        2695                2700                2705 atg gcc gta gct gac cag gcc gat ggc cat ggt cag cgc acc atc gag     10255
Met Ala Val Ala Asp Gln Ala Asp Gly His Gly Gln Arg Thr Ile Glu
        2710                2715                2720 gac ctg cgc cgc gcc tat gac ctg cgc ctg cag cag gtc gag ggc acg     10303
Asp Leu Arg Arg Ala Tyr Asp Leu Arg Leu Gln Gln Val Glu Gly Thr
    2725                2730                2735 cgg gcc gcg tct ggt ccg gtc ggg gcg cat gaa gaa gcg ctt gcc ccg     10351
Arg Ala Ala Ser Gly Pro Val Gly Ala His Glu Glu Ala Leu Ala Pro
2740                2745                2750                2755 cca tcg acc aac ccg ttc cag tcg cgt ggc tac ggg cat cag gtg gaa     10399
Pro Ser Thr Asn Pro Phe Gln Ser Arg Gly Tyr Gly His Gln Val Glu
            2760                2765                2770 ctg ggc gcg ccg gtg acc ggt ggc tcc tac agt gcc gag gcg gca tcg     10447
Leu Gly Ala Pro Val Thr Gly Gly Ser Tyr Ser Ala Glu Ala Ala Ser
        2775                2780                2785 ccc gat acg tcg gac cag atg ctc tcc tcc att gct ggc cag atc cac     10495
Pro Asp Thr Ser Asp Gln Met Leu Ser Ser Ile Ala Gly Gln Ile His
        2790                2795                2800 acg ctg cgt gaa aac ctt gca ccc tcc att gat ggt ggg ctg ggc ttc     10543
Thr Leu Arg Glu Asn Leu Ala Pro Ser Ile Asp Gly Gly Leu Gly Phe
    2805                2810                2815 cgg tcg cgt tcg ggc gag cat ggc atg ggc cgc ctg acg gaa gcg aac     10591
Arg Ser Arg Ser Gly Glu His Gly Met Gly Arg Leu Thr Glu Ala Asn
2820                2825                2830                2835 att ccc atc gtg ggc cgc ctg ccg ctg cag gcc ggt gct tcc gcc ctg     10639
Ile Pro Ile Val Gly Arg Leu Pro Leu Gln Ala Gly Ala Ser Ala Leu
            2840                2845                2850 acc ttc tcg atc acg cca acc atg atc tgg tcg ggc cag ctc aac aca     10687
Thr Phe Ser Ile Thr Pro Thr Met Ile Trp Ser Gly Gln Leu Asn Thr
        2855                2860                2865 ggc tcc gtc tat gat gtg ccg cgt tat ggc acg ttc atg gca acg cag     10735
Gly Ser Val Tyr Asp Val Pro Arg Tyr Gly Thr Phe Met Ala Thr Gln
        2870                2875                2880 gct gcc aac cag tgc gcg ggc cac agt tcg tgt ggc ggg ctt gat ttc     10783
Ala Ala Asn Gln Cys Ala Gly His Ser Ser Cys Gly Gly Leu Asp Phe
    2885                2890                2895 ctg agc gcc aac cat acc cag cgc atc gcg gct ggt gca ggc gag gcc     10831
Leu Ser Ala Asn His Thr Gln Arg Ile Ala Ala Gly Ala Gly Glu Ala
2900                2905                2910                2915 ggg ttt gcg ccg gat gtg cag ttc ggc aat agc tgg gtg cgc gct gat     10879
Gly Phe Ala Pro Asp Val Gln Phe Gly Asn Ser Trp Val Arg Ala Asp
            2920                2925                2930 gtc tgc gcc tcg ccc atc ggc ttc ccc att acc aac gtg ctg ggc ggg     10927
Val Cys Ala Ser Pro Ile Gly Phe Pro Ile Thr Asn Val Leu Gly Gly
        2935                2940                2945 gtc gag ttc tcg ccg cgc gtg ggg ccg gtc acg ttc cgt gtc agc gcc     10975
```

-continued

```
Val Glu Phe Ser Pro Arg Val Gly Pro Val Thr Phe Arg Val Ser Ala
    2950                2955                2960 gag cgc cgg tcg atc acc aac agc gtg ctg tcc tat ggt ggc ctg cgt    11023
Glu Arg Arg Ser Ile Thr Asn Ser Val Leu Ser Tyr Gly Gly Leu Arg
    2965                2970                2975 gat ccg aac tac aac agc gag gtc ggt cgt tac gcg cgt cag gtc tat    11071
Asp Pro Asn Tyr Asn Ser Glu Val Gly Arg Tyr Ala Arg Gln Val Tyr
2980                2985                2990                2995 ggt cat gac ctg acc aag cag tgg ggt agc gaa tgg ggt ggg gtg gtg    11119
Gly His Asp Leu Thr Lys Gln Trp Gly Ser Glu Trp Gly Gly Val Val
            3000                3005                3010 acc aac cac ttc cac ggt cag gtc gag gcg acg ctg ggc aac acc atc    11167
Thr Asn His Phe His Gly Gln Val Glu Ala Thr Leu Gly Asn Thr Ile
            3015                3020                3025 ctg tat ggt ggt ggc ggc tac gcg atc cag acc ggc aag aac gtg cag    11215
Leu Tyr Gly Gly Gly Gly Tyr Ala Ile Gln Thr Gly Lys Asn Val Gln
            3030                3035                3040 cgc aac agc gag cgc gaa gcc ggc atc ggc gcc aat acg ctg gtg tgg    11263
Arg Asn Ser Glu Arg Glu Ala Gly Ile Gly Ala Asn Thr Leu Val Trp
    3045                3050                3055 cat aac gcc aac atg ctg gtg cgc att ggc gtg agc ctg acc tat ttc    11311
His Asn Ala Asn Met Leu Val Arg Ile Gly Val Ser Leu Thr Tyr Phe
3060                3065                3070                3075 ggt tat gcc cat aac gag gat ttc tat acc tat ggg cag ggc ggc tac    11359
Gly Tyr Ala His Asn Glu Asp Phe Tyr Thr Tyr Gly Gln Gly Gly Tyr
            3080                3085                3090 ttc tcg ccg cag tcc tat tat gcg gca acc gtg ccg gtg cgt tat gcg    11407
Phe Ser Pro Gln Ser Tyr Tyr Ala Ala Thr Val Pro Val Arg Tyr Ala
            3095                3100                3105 ggc cag cac aag cgg ctg gac tgg gat gtg acg ggt agc gtg ggc tac    11455
Gly Gln His Lys Arg Leu Asp Trp Asp Val Thr Gly Ser Val Gly Tyr
            3110                3115                3120 cag gtg ttc cat gaa cac gcg gcg ccc ttc ttc ccc acg tca tcg ctg    11503
Gln Val Phe His Glu His Ala Ala Pro Phe Phe Pro Thr Ser Ser Leu
    3125                3130                3135 ctg cag tcc ggt gcc aat tac gtt gca tcg aac ttt gtg cag aat gcc    11551
Leu Gln Ser Gly Ala Asn Tyr Val Ala Ser Asn Phe Val Gln Asn Ala
3140                3145                3150                3155 ctg cca acg gat tat ctg tcg cag gaa acg gtg aac agc gcc tac tat    11599
Leu Pro Thr Asp Tyr Leu Ser Gln Glu Thr Val Asn Ser Ala Tyr Tyr
            3160                3165                3170 ccc ggg gat agt att gct ggt ctt acg ggc ggc ttt aat gct agg gtg    11647
Pro Gly Asp Ser Ile Ala Gly Leu Thr Gly Gly Phe Asn Ala Arg Val
            3175                3180                3185 ggc tat cgc ttt aca cgc aat gtt cgt ctt gat ctc tcg ggg cgc tat    11695
Gly Tyr Arg Phe Thr Arg Asn Val Arg Leu Asp Leu Ser Gly Arg Tyr
            3190                3195                3200 cag aag gcc ggt aac tgg act gaa agc ggc gcc atg att tcc gca cac    11743
Gln Lys Ala Gly Asn Trp Thr Glu Ser Gly Ala Met Ile Ser Ala His
    3205                3210                3215 tat ctt att atg gac cag ta atg aca act ttg aac gca aaa ccg gac    11790
Tyr Leu Ile Met Asp Gln     Met Thr Thr Leu Asn Ala Lys Pro Asp
3220                3225                3230 ttt tcg ctt ttc ctg cag gca ctg tcc tgg gag atc gat gat cag gcc    11838
Phe Ser Leu Phe Leu Gln Ala Leu Ser Trp Glu Ile Asp Asp Gln Ala
3235                3240                3245                3250 ggg atc gag gtc agg aat gac ctg ttg cgc gag gtc ggc cgg ggt atg    11886
Gly Ile Glu Val Arg Asn Asp Leu Leu Arg Glu Val Gly Arg Gly Met
            3255                3260                3265
```

-continued

| | |
|---|---|
| gct ggt cgt ttc cag ccg ccg ctg tgc aac acc atc cac cag ctc cag<br>Ala Gly Arg Phe Gln Pro Pro Leu Cys Asn Thr Ile His Gln Leu Gln<br>          3270                    3275                  3280 | 11934 |
| atc gag ctg aac gcc ctg ctg gcc atg atc aac tgg ggc tac gta aag<br>Ile Glu Leu Asn Ala Leu Leu Ala Met Ile Asn Trp Gly Tyr Val Lys<br>3285                    3290                    3295 | 11982 |
| ctg gac ctg ctg gcg gaa gaa cag gcc atg cgc atc gtg cat gaa gac<br>Leu Asp Leu Leu Ala Glu Glu Gln Ala Met Arg Ile Val His Glu Asp<br>          3300                    3305                  3310 | 12030 |
| ctg ccg cag gtg ggc agc gcg ggc gaa ccc gcc ggc aca tgg ctt gcc<br>Leu Pro Gln Val Gly Ser Ala Gly Glu Pro Ala Gly Thr Trp Leu Ala<br>3315                    3320                    3325                  3330 | 12078 |
| ccg gtg ctg gaa ggg ctt tat ggc cgc tgg atc acg tcg cag ccc ggc<br>Pro Val Leu Glu Gly Leu Tyr Gly Arg Trp Ile Thr Ser Gln Pro Gly<br>                    3335                    3340                  3345 | 12126 |
| gcc ttc ggt gat tat gtc gtg acg cgt gat atc gac gcg gaa gac ctg<br>Ala Phe Gly Asp Tyr Val Val Thr Arg Asp Ile Asp Ala Glu Asp Leu<br>          3350                    3355                  3360 | 12174 |
| aac tcg gtc ccg gcc cag acg gtc atc ctg tac atg cgc acc cgc agc<br>Asn Ser Val Pro Ala Gln Thr Val Ile Leu Tyr Met Arg Thr Arg Ser<br>3365                    3370                    3375 | 12222 |
| gcc gcg acc tgaccttacc agtcgcgcca tttgcgtcaa aaccctgccc<br>Ala Ala Thr<br>  3380 | 12271 |
| acaggcgtgt tcatgccctg taggcggggt ttttgcgtat atggcctcca ctctttgccc | 12331 |
| tgttttttgcg ctagatcatg cggcgtgggg gcagggtgct tcacaaatgg gccaaggaga | 12391 |
| tggcgggcgg ctgcccgtgt cgtcactgtc cagcccctga aggaggagcc agccac atg<br>                                                                                         Met | 12450 |
| aga ctg tcc cgc aag ata ttc ctg tta tcc gcc gtg gcg tgt ggc atg<br>Arg Leu Ser Arg Lys Ile Phe Leu Leu Ser Ala Val Ala Cys Gly Met<br>          3385                    3390                    3395 | 12498 |
| gcg ctg gcc cag gcg ccc gcc ttt gcc cgg cat gcg cat gat ggc ggg<br>Ala Leu Ala Gln Ala Pro Ala Phe Ala Arg His Ala His Asp Gly Gly<br>   3400                    3405                    3410 | 12546 |
| ggc gac cag gcc gat gcc cgg gcg cgg cag gtg ctc gcc tcc atg agc<br>Gly Asp Gln Ala Asp Ala Arg Ala Arg Gln Val Leu Ala Ser Met Ser<br>3415                    3420                    3425                  3430 | 12594 |
| ctt gag gac aag atg tcc ctg ctg ttc agt gtt gat ggc ggc ggc ttt<br>Leu Glu Asp Lys Met Ser Leu Leu Phe Ser Val Asp Gly Gly Gly Phe<br>                    3435                    3440                  3445 | 12642 |
| aac ggc agc gtg gcc cct ccc ggt ggc ctg ggg tcg gct gca tac ctg<br>Asn Gly Ser Val Ala Pro Pro Gly Gly Leu Gly Ser Ala Ala Tyr Leu<br>          3450                    3455                    3460 | 12690 |
| cgc gcg ccc cag ggt tcg ggc ctg cct gac ctg cag att tcg gat gcg<br>Arg Ala Pro Gln Gly Ser Gly Leu Pro Asp Leu Gln Ile Ser Asp Ala<br>3465                    3470                    3475 | 12738 |
| ggg ctt ggc gtg cgc aac ccc gcg cat atc cgc agg aat ggt gaa gcg<br>Gly Leu Gly Val Arg Asn Pro Ala His Ile Arg Arg Asn Gly Glu Ala<br>                    3480                    3485                  3490 | 12786 |
| gtt tcg ctg ccg tcg ggc cag tcc acg gcc agt acg tgg gat atg gac<br>Val Ser Leu Pro Ser Gly Gln Ser Thr Ala Ser Thr Trp Asp Met Asp<br>3495                    3500                    3505                  3510 | 12834 |
| atg gcg cgg cag gcc ggt gtc atg atc ggg cgc gag gca tgg cag agc<br>Met Ala Arg Gln Ala Gly Val Met Ile Gly Arg Glu Ala Trp Gln Ser<br>                    3515                    3520                  3525 | 12882 |
| ggc ttc aac atc ctg ctt ggc ggc ggt gcg gac ctg acg cgc gac ccg<br>Gly Phe Asn Ile Leu Leu Gly Gly Gly Ala Asp Leu Thr Arg Asp Pro<br>          3530                    3535                  3540 | 12930 |

-continued

| | |
|---|---|
| cgt ggc ggc cgc aac ttt gaa tat gcg ggc gaa gat ccg ctg cag acc<br>Arg Gly Gly Arg Asn Phe Glu Tyr Ala Gly Glu Asp Pro Leu Gln Thr<br>    3545                3550                3555 | 12978 |
| ggg cgc atg gtg ggc agc acc att gca ggc gtg cag tcg cag cat gtg<br>Gly Arg Met Val Gly Ser Thr Ile Ala Gly Val Gln Ser Gln His Val<br>3560                3565                3570 | 13026 |
| atc tcc acg ctc aag cat tat gcg atg aat gac ctc gaa acc tcg cgc<br>Ile Ser Thr Leu Lys His Tyr Ala Met Asn Asp Leu Glu Thr Ser Arg<br>3575                3580                3585                3590 | 13074 |
| atg acc atg agc gcg gat atc gac cct gtg gcc atg cgt gaa agc gac<br>Met Thr Met Ser Ala Asp Ile Asp Pro Val Ala Met Arg Glu Ser Asp<br>                3595                3600                3605 | 13122 |
| ctg ctg ggc ttc gag atc gcg ctt gaa acc ggg cat ccg ggc gcg gtc<br>Leu Leu Gly Phe Glu Ile Ala Leu Glu Thr Gly His Pro Gly Ala Val<br>            3610                3615                3620 | 13170 |
| atg tgc tcg tac aac cgc gtc aac gac ctg tat gcg tgt gaa aac ccg<br>Met Cys Ser Tyr Asn Arg Val Asn Asp Leu Tyr Ala Cys Glu Asn Pro<br>        3625                3630                3635 | 13218 |
| tac ctg ctg aac aag acg ctg aag cag gac tgg cat tat ccc ggc ttt<br>Tyr Leu Leu Asn Lys Thr Leu Lys Gln Asp Trp His Tyr Pro Gly Phe<br>    3640                3645                3650 | 13266 |
| gtc atg tcc gac tgg ggg gcc acg cat tcc tcc gcg cgg gcg gcg ctg<br>Val Met Ser Asp Trp Gly Ala Thr His Ser Ser Ala Arg Ala Ala Leu<br>3655                3660                3665                3670 | 13314 |
| gcg ggg ctg gat cag gaa tcc gca ggt gac cat acg gat gcc cgg ccc<br>Ala Gly Leu Asp Gln Glu Ser Ala Gly Asp His Thr Asp Ala Arg Pro<br>                3675                3680                3685 | 13362 |
| tat ttc cgc acc ctg ctg gct gct gac gtc aag gcc gga cgc gtg ccc<br>Tyr Phe Arg Thr Leu Leu Ala Ala Asp Val Lys Ala Gly Arg Val Pro<br>            3690                3695                3700 | 13410 |
| gaa gcg cgc atc aac gac atg gcg gag cgc gtt gtc cgc gcg ctg ttc<br>Glu Ala Arg Ile Asn Asp Met Ala Glu Arg Val Val Arg Ala Leu Phe<br>        3705                3710                3715 | 13458 |
| gcg gcg ggg ctt gtg gac cat ccg gcg cag cgc ggg ccg ctt gat gtc<br>Ala Ala Gly Leu Val Asp His Pro Ala Gln Arg Gly Pro Leu Asp Val<br>    3720                3725                3730 | 13506 |
| gtg acc gat acc ctc gtg gcc cag aag gat gag gaa gaa ggc gcg gtc<br>Val Thr Asp Thr Leu Val Ala Gln Lys Asp Glu Glu Glu Gly Ala Val<br>3735                3740                3745                3750 | 13554 |
| ctg ctg cgc aac cag ggc aac atc ctg ccg ctt tcg cct acc gcg cgc<br>Leu Leu Arg Asn Gln Gly Asn Ile Leu Pro Leu Ser Pro Thr Ala Arg<br>                3755                3760                3765 | 13602 |
| att gcc gtc att ggt ggc cat gcc gat gcg ggc gtg att tcg ggc ggt<br>Ile Ala Val Ile Gly Gly His Ala Asp Ala Gly Val Ile Ser Gly Gly<br>            3770                3775                3780 | 13650 |
| ggc tcc agc cag gtc gat ccc atc ggg ggc gag gcg gtg aag ggg ccg<br>Gly Ser Ser Gln Val Asp Pro Ile Gly Gly Glu Ala Val Lys Gly Pro<br>        3785                3790                3795 | 13698 |
| ggc aag aag gaa tgg ccg ggt gat ccg gtc tat ttc ccg tcc tcg ccg<br>Gly Lys Lys Glu Trp Pro Gly Asp Pro Val Tyr Phe Pro Ser Ser Pro<br>    3800                3805                3810 | 13746 |
| ctc aag gcc atg cag gcc gag gcg ccc ggt gcc cgg atc acc tat gat<br>Leu Lys Ala Met Gln Ala Glu Ala Pro Gly Ala Arg Ile Thr Tyr Asp<br>3815                3820                3825                3830 | 13794 |
| ccc ggc acc agt atc gcc tct gcc gtg cgg gcc gcg cgg gcg gct gac<br>Pro Gly Thr Ser Ile Ala Ser Ala Val Arg Ala Ala Arg Ala Ala Asp<br>                3835                3840                3845 | 13842 |
| gtg gtg gtg gta tat gcc acg cag ttc acc ttc gag ggg atg gac gcg<br>Val Val Val Val Tyr Ala Thr Gln Phe Thr Phe Glu Gly Met Asp Ala<br>            3850                3855                3860 | 13890 |

-continued

```
ccc agc atg cac ctt gat gac aat gcc gat gcg ctg att acg gcc gtg         13938
Pro Ser Met His Leu Asp Asp Asn Ala Asp Ala Leu Ile Thr Ala Val
    3865                3870                3875 gcc gcc gcc aac ccg cgc acg gtg gtg gtg atg gaa acc ggc gac ccg         13986
Ala Ala Ala Asn Pro Arg Thr Val Val Val Met Glu Thr Gly Asp Pro
    3880                3885                3890 gtg ctg atg ccg tgg aac agc agc gtg gcg ggc gtg ctc gag gca tgg         14034
Val Leu Met Pro Trp Asn Ser Ser Val Ala Gly Val Leu Glu Ala Trp
3895                3900                3905                3910 ttc ccc ggt tcg ggc ggt ggt ccg gcc att gcc cgg ctg ctg ttt ggc         14082
Phe Pro Gly Ser Gly Gly Gly Pro Ala Ile Ala Arg Leu Leu Phe Gly
            3915                3920                3925 aag gtt gcg ccc tcg ggc cac ctg acc atg acc ttc ccg cag gcg gaa         14130
Lys Val Ala Pro Ser Gly His Leu Thr Met Thr Phe Pro Gln Ala Glu
    3930                3935                3940 tct cag ctg gcc cac ccc gat att gca ggt gtt acg gca gat aac gtg         14178
Ser Gln Leu Ala His Pro Asp Ile Ala Gly Val Thr Ala Asp Asn Val
    3945                3950                3955 ttc gag atg cag ttc cat acc gat cag gaa ctg gtt tac gac gaa ggc         14226
Phe Glu Met Gln Phe His Thr Asp Gln Glu Leu Val Tyr Asp Glu Gly
    3960                3965                3970 agc gat gtc ggt tat cgc tgg ttc gac cgc aat cac ttc aag ccg ctc         14274
Ser Asp Val Gly Tyr Arg Trp Phe Asp Arg Asn His Phe Lys Pro Leu
3975                3980                3985                3990 tat ccg ttc ggt tat ggc ctg acc tac acc acg ttc agc acc gat ggg         14322
Tyr Pro Phe Gly Tyr Gly Leu Thr Tyr Thr Thr Phe Ser Thr Asp Gly
            3995                4000                4005 ctg aag gtg acg gaa cgc cat ggg cag gtt acg gcc acg ttc aac gtg         14370
Leu Lys Val Thr Glu Arg His Gly Gln Val Thr Ala Thr Phe Asn Val
    4010                4015                4020 cac aac acc ggc acg cgg gcg ggc gtg gat gtt ccg cag gtc tat gtt         14418
His Asn Thr Gly Thr Arg Ala Gly Val Asp Val Pro Gln Val Tyr Val
    4025                4030                4035 ggc ctg ccc gat ggt ggc gcg cgc cgc ctg gcg ggc tgg cag cgc atc         14466
Gly Leu Pro Asp Gly Gly Ala Arg Arg Leu Ala Gly Trp Gln Arg Ile
    4040                4045                4050 agc ctg gcg ccg ggc gag agc cgt cag gtt tcc gtg cag ctt gag ccg         14514
Ser Leu Ala Pro Gly Glu Ser Arg Gln Val Ser Val Gln Leu Glu Pro
4055                4060                4065                4070 cgc ctg ctg gcc cat ttc gat gga aaa cat gac cgg tgg agc gtg ccc         14562
Arg Leu Leu Ala His Phe Asp Gly Lys His Asp Arg Trp Ser Val Pro
            4075                4080                4085 tcg ggc acc ttc cgc gtg tgg ctt gcg tca tgc gcc acc gat gac agc         14610
Ser Gly Thr Phe Arg Val Trp Leu Ala Ser Cys Ala Thr Asp Asp Ser
    4090                4095                4100 cag cag acc acc atg cat ctg cat ggc cgg acc atg gcg ccc                 14652
Gln Gln Thr Thr Met His Leu His Gly Arg Thr Met Ala Pro
    4105                4110                4115 tgagggtgga tgtcatgggc agggggtat gtgtagcggc gatgatgggg gcgggcctgc        14712
tgcctgccag cccatgctg gcggccagcc tttcatggtc cgatacgcca gccgagcgcg        14772
cgcgcctgat gatgagcgtg caggaactgg aaataaccct gctcacccac cccagcgcca      14832
cgctggcgct ggaggactgg tgcgctaccc accatatggc agcacgcccc gttgtcgtgg      14892
cgcagaaggt cgccctgccg cagcccgacc ccgtgcccgc gcgggtgcgg ccgatctgg       14952 gcgtgagtgc tgcgcaaccg gtgcggcacc ggcaggtgcg gctggtctgc gggccatatg      15012
tgctttcggt ggcggataac tggtatgtgc ccgccctgct gaccccgcag atgaacgcca      15072
```

-continued

```
cgctggaggg aaccgacaca tccttcggcc atgtggtggc gccgctgcac tttacgcgcg        15132
agcggctgga gtttacgcgg ctgtggtcgc catggccggg accggttgtg gggcagggcg        15192
gcacgatgat cgtggctccg gctgaaatcg tgcgccagcg cgcggtactg cgtgacggcc        15252
agggccgtcc gttcagcgag gtggtggaaa cctataccga ccagaccctc gcttttacgc        15312
ctcagggcca gaggtaaagc tttcctccaa aaagctttaa agaacgctgc cttttgaaa        15372 aaaggcggca cccggaaact tttattctct gttccctgc cgtttgcagc ctggcggcag        15432
gagggctacg ccggagcatg cgatcatgac cggagccaga accccatga cagatttgcg        15492 agatcccaac accctgccg agaccgtgcg gcagctactg ggcctgcaac cccaccccga        15552
aggcggcagc taccgcgaac tatggcgcga taccccgccc gatggcccgc gtggcgcggt        15612
ctcgaccatc agtttcctgc tggcggcagg cgagcgctcg cactggcacc gcgttgatgc        15672
agccgagatc tggtgctggc agggtggcgg cccgcttgtg ctggaaattg ccgcaaggca        15732
gggtgccgng atcgagcgga tcgtgcttgg cccgntgcca gcacgggggc aggtgttgca        15792
ggcggtggtg ccaccgggcg catggcaggc ggctcagagc gaggggggcgt ggagccttat        15852 gggctgccag gtggcccccg ccttcgtttt cagccagttt gaactggccc cgcccggctg        15912
gacgccacaa ggagacaatg catgacaacc ccgcaatggc tcatctgggc ccgtgacctg        15972
caggcgctgg cccagagcgg cctgacctat gccgaaagcc cgttcgaccg cgaacgttat        16032
gaaagcataa ggcagatcgc agccgatatg atggccgcgg gcagtcatgc cgacatggag        16092
cgcgtgctcg acctgttcac cagtcaggac ggctatgcca cgcccaagct ggtggtgcgc        16152
gccgccgtgt ttgatgcgca gggccgcatg ctgctggtgc gcgaggtgct ggaccatgac        16212
cgctggaccc tgccgggcgg ctgggcggat gtaaacctga ccccggtgga aaatacggta        16272
aaggaagtgc gcgaggaaag cggctttagc gtgcgcgtga ccaagctcgc cgccgtgtgg        16332
gaccgcgacc ggcagggcca tccgcccgca ccctttttcat gctgcacgct ttgtttcatc        16392
tgcgaactga ccggtgggag cgccgagacc agtatcgaga catcggagat tggctggttt        16452
gcagccgaca gcctgcctac cgacttgtcg cttgggcgcg tgctgcccca tcagctgacc        16512
cgcatgttag aacatgccgc caaccccgac ctgcccaggg attttgatta aaatcgttta        16572
aagacaatgt attggtgaaa gcaggaaagg tttttgggtg tcgcctttt tcaaagggt        16632 ggcatttggc caggccggtc agcaagcagt ctcaccctgc atggcttgcg ggcgctgtgc        16692
atgcaggcca ttgaaaaaacc gaccgggatt tccatatcca atacaaattg taacctgatg        16752
cagtgcaaca gacagactgg ataagccatg accgaacaga ccaccacgac cccaccccgaa        16812 gccacgggcg aacagcatga attc                                              16836
```

<210> SEQ ID NO: 2
<211> LENGTH: 341
<212> TYPE: PRT
<213> ORGANISM: Acetobacter xylinum
<220> FEATURE:
<223> OTHER INFORMATION: n at positions 15741 and 15767 may be a, g, t, or c

<400> SEQUENCE: 2

Met Ala Val Ala Gly Ser Phe Pro Met Leu Ser Ser Gly Ala Glu Ala
 1               5                  10                  15

Asp Asp Ala Ile Gly Ile Asn Pro Gln Ile Ala Gln Gln Trp Ala Ile
             20                  25                  30

Phe Arg Asp Lys Tyr Phe His Pro Asn Gly Arg Ile Ile Asp Thr Gly
         35                  40                  45

-continued

```
Asn Ser Gly Glu Ser His Ser Glu Gly Gln Gly Tyr Gly Met Leu Phe
        50                  55                  60
Ser Ala Ala Ala Gly Asp Gln Ala Ala Phe Glu Val Ile Trp Val Trp
 65                  70                  75                  80
Ala Arg Thr Asn Leu Gln His Lys Asp Asp Ala Leu Phe Ser Trp Arg
                 85                  90                  95
Tyr Leu Asp Gly His Lys Pro Pro Val Ala Asp Lys Asn Asn Ala Thr
                100                 105                 110
Asp Gly Asp Leu Leu Ile Ala Leu Ala Leu Ala Trp Ala Gly Lys Arg
            115                 120                 125
Trp Lys Arg Ala Asp Tyr Ile Gln Asp Ala Met Asn Ile Tyr Gly Asp
        130                 135                 140
Val Leu Lys Leu Met Thr Lys Ser Val Gly Pro Tyr Thr Val Leu Leu
145                 150                 155                 160
Pro Gly Ala Val Gly Phe Leu Thr Lys Asp Thr Val Thr Leu Asn Leu
                165                 170                 175
Ser Tyr Tyr Val Met Pro Ser Leu Met Gln Ala Phe Ala Leu Thr Gly
                180                 185                 190
Asp Ala Lys Trp Thr Lys Val Met Gly Asp Gly Leu Gln Ile Ile Ala
            195                 200                 205
Lys Gly Arg Phe Gly Glu Trp Lys Leu Pro Pro Asp Trp Leu Ser Ile
        210                 215                 220
Asn Leu His Thr Asn Ala Phe Ser Ile Ala Lys Gly Trp Pro Pro Arg
225                 230                 235                 240
Phe Ser Tyr Asp Ala Ile Arg Val Pro Leu Tyr Leu Ser Trp Ala His
                245                 250                 255
Met Leu Thr Pro Glu Leu Leu Ala Asp Phe Ser Arg Phe Trp Asn His
                260                 265                 270
Tyr Gly Ala Ser Ala Leu Pro Gly Trp Val Asp Leu Thr Asn Gly Ala
            275                 280                 285
Arg Ser Pro Tyr Asn Ala Pro Pro Gly Tyr Leu Ala Val Ala Ser Cys
        290                 295                 300
Thr Gly Leu Ala Ser Ala Gly Glu Leu Pro Thr Leu Asp His Ala Pro
305                 310                 315                 320
Asp Tyr Tyr Ser Ala Ala Leu Thr Met Leu Ala Tyr Ile Ala Arg Asn
                325                 330                 335
Gln Gly Asp Gly Met
            340

<210> SEQ ID NO: 3
<211> LENGTH: 756
<212> TYPE: PRT
<213> ORGANISM: Acetobacter xylinum
<220> FEATURE:
<223> OTHER INFORMATION: n at positions 15741 and 15767 may be a, g, t,
      or c

<400> SEQUENCE: 3

Met Ser Glu Val Gln Ser Pro Val Pro Thr Glu Ser Arg Leu Gly Arg
 1               5                  10                  15
Ile Ser Asn Lys Ile Leu Ser Leu Arg Gly Ala Ser Tyr Ile Val Gly
                 20                  25                  30
Ala Leu Gly Leu Cys Ala Leu Ile Ala Ala Thr Thr Val Thr Leu Asn
             35                  40                  45
Asn Asn Glu Gln Leu Ile Val Ala Ala Val Cys Val Val Ile Phe Phe
```

-continued

```
            50                  55                  60
    Val Val Gly Arg Gly Lys Ser Arg Arg Thr Gln Ile Phe Leu Glu Val
    65                  70                  75                  80

Leu Ser Ala Leu Val Ser Leu Arg Tyr Leu Thr Trp Arg Leu Thr Glu
                        85                  90                  95

Thr Leu Asp Phe Asn Thr Trp Ile Gln Gly Ile Leu Gly Val Ile Leu
                       100                 105                 110

Leu Met Ala Glu Leu Tyr Ala Leu Tyr Met Leu Phe Leu Ser Tyr Phe
                       115                 120                 125

Gln Thr Ile Gln Pro Leu His Arg Ala Pro Leu Pro Leu Pro Asp Asn
                       130                 135                 140

Val Asp Asp Trp Pro Thr Val Asp Ile Phe Ile Pro Thr Tyr Asp Glu
    145                 150                 155                 160

Gln Leu Ser Ile Val Arg Leu Thr Val Leu Gly Ala Leu Gly Ile Asp
                       165                 170                 175

Trp Pro Pro Asp Lys Val Asn Val Tyr Ile Leu Asp Asp Gly Val Arg
                       180                 185                 190

Pro Glu Phe Glu Gln Phe Ala Lys Asp Cys Gly Ala Leu Tyr Ile Gly
                       195                 200                 205

Arg Val Asp Val Asp Ser Ala His Ala Lys Ala Gly Asn Leu Asn His
                       210                 215                 220

Ala Ile Lys Arg Thr Ser Gly Asp Tyr Ile Leu Ile Leu Asp Cys Asp
    225                 230                 235                 240

His Ile Pro Thr Arg Ala Phe Leu Gln Ile Ala Met Gly Trp Met Val
                       245                 250                 255

Ala Asp Arg Lys Ile Ala Leu Met Gln Thr Pro His His Phe Tyr Ser
                       260                 265                 270

Pro Asp Pro Phe Gln Arg Asn Leu Ala Val Gly Tyr Arg Thr Pro Pro
                       275                 280                 285

Glu Gly Asn Leu Phe Tyr Gly Val Ile Gln Asp Gly Asn Asp Phe Trp
                       290                 295                 300

Asp Ala Thr Phe Phe Cys Gly Ser Cys Ala Ile Leu Arg Arg Glu Ala
    305                 310                 315                 320

Ile Glu Ser Ile Gly Gly Phe Ala Val Glu Thr Val Thr Glu Asp Ala
                       325                 330                 335

His Thr Ala Leu Arg Met Gln Arg Arg Gly Trp Ser Thr Ala Tyr Leu
                       340                 345                 350

Arg Ile Pro Val Ala Ser Gly Leu Ala Thr Glu Arg Leu Thr Thr His
                       355                 360                 365

Ile Gly Gln Arg Met Arg Trp Ala Arg Gly Met Ile Gln Ile Phe Arg
                       370                 375                 380

Val Asp Asn Pro Met Leu Gly Arg Gly Leu Lys Leu Gly Gln Arg Leu
    385                 390                 395                 400

Cys Tyr Leu Ser Ala Met Thr Ser Phe Phe Ala Ile Pro Arg Val
                       405                 410                 415

Ile Phe Leu Ala Ser Pro Leu Ala Leu Phe Ala Gly Gln Asn Ile
                       420                 425                 430

Ile Ala Ala Ala Pro Leu Ala Val Ala Ala Tyr Ala Leu Pro His Met
                       435                 440                 445

Phe His Ser Ile Ala Thr Ala Ala Lys Val Asn Lys Gly Trp Arg Tyr
                       450                 455                 460

Ser Phe Trp Ser Glu Val Tyr Glu Thr Thr Met Ala Leu Phe Leu Val
    465                 470                 475                 480
```

```
Arg Val Thr Ile Val Thr Leu Leu Phe Pro Ser Lys Gly Lys Phe Asn
            485                 490                 495
Val Thr Glu Lys Gly Gly Val Leu Glu Glu Glu Phe Asp Leu Gly
            500                 505                 510
Ala Thr Tyr Pro Asn Ile Ile Phe Ala Thr Ile Met Met Gly Gly Leu
            515                 520                 525
Leu Ile Gly Leu Phe Glu Leu Ile Val Arg Phe Asn Gln Leu Asp Val
            530                 535                 540
Ile Ala Arg Asn Ala Tyr Leu Leu Asn Cys Ala Trp Ala Leu Ile Ser
545                 550                 555                 560
Leu Ile Ile Leu Phe Ala Ala Ile Ala Val Gly Arg Glu Thr Lys Gln
                565                 570                 575
Val Arg Tyr Asn His Arg Val Glu Ala His Ile Pro Val Thr Val Tyr
            580                 585                 590
Asp Ala Pro Ala Glu Gly Gln Pro His Thr Tyr Tyr Asn Ala Thr His
            595                 600                 605
Gly Met Thr Gln Asp Val Ser Met Gly Gly Val Ala Val His Ile Pro
            610                 615                 620
Leu Pro Asp Val Thr Thr Gly Pro Val Lys Lys Arg Ile His Ala Val
625                 630                 635                 640
Leu Asp Gly Glu Glu Ile His Ile Pro Ala Thr Met Leu Arg Cys Thr
                645                 650                 655
Asn Gly Lys Ala Val Phe Thr Trp Asp Asn Asn Asp Leu Asp Thr Glu
            660                 665                 670
Arg Asp Ile Val Arg Phe Val Phe Gly Arg Ala Asp Ala Trp Leu Gln
            675                 680                 685
Trp Asn Asn Tyr Glu Asp Asp Arg Pro Leu Arg Ser Leu Trp Ser Leu
            690                 695                 700
Leu Leu Ser Ile Lys Ala Leu Phe Arg Lys Lys Gly Lys Ile Met Ala
705                 710                 715                 720
Asn Ser Arg Pro Lys Lys Lys Pro Leu Ala Leu Pro Val Glu Arg Arg
                725                 730                 735
Glu Pro Thr Thr Ile His Ser Gly Gln Thr Gln Glu Gly Lys Ile Ser
            740                 745                 750
Arg Ala Ala Ser
        755

<210> SEQ ID NO: 4
<211> LENGTH: 802
<212> TYPE: PRT
<213> ORGANISM: Acetobacter xylinum
<220> FEATURE:
<223> OTHER INFORMATION: n at positions 15741 and 15767 may be a, g, t,
      or c

<400> SEQUENCE: 4

Met Lys Met Val Ser Leu Ile Ala Leu Leu Val Phe Ala Thr Gly Ala
1               5                   10                  15
Gln Ala Ala Pro Val Ala Ser Lys Ala Pro Ala Pro Gln Pro Ala Gly
                20                  25                  30
Ser Asp Leu Pro Pro Leu Pro Ala Ala Pro Pro Gln Ala Pro Pro
            35                  40                  45
Ala Ala Ala Ser Ala Ala Pro Pro Ala Thr Thr Pro Ala Ala Asp Ala
        50                  55                  60
Ser Ala Ala Ser Ala Ala Asp Ala Val Val Asp Asn Ala Glu Asn Ala
```

```
              65                  70                  75                  80
    Ile Ala Gly Ser Asp Val Ala Thr Val His Thr Tyr Ser Leu Arg Glu
                        85                  90                  95
    Leu Gly Ala Gln Ser Ala Leu Lys Met Gln Gly Ala Ala Thr Leu Gln
                    100                 105                 110
    Gly Leu Gln Phe Gly Ile Pro Ala Asp Gln Leu Val Thr Ser Ala Arg
                    115                 120                 125
    Leu Val Val Ser Gly Ala Met Ser Pro Ser Leu Gln Pro Asp Thr Ser
        130                 135                 140
    Ala Val Thr Ile Thr Leu Asn Glu Gln Phe Ile Gly Thr Leu Arg Pro
    145                 150                 155                 160
    Asp Pro Thr His Pro Thr Phe Gly Pro Leu Ser Phe Asp Ile Asn Pro
                    165                 170                 175
    Ile Phe Phe Ile Ser Gly Asn Arg Leu Asn Phe Ser Phe Ala Ser Ser
                    180                 185                 190
    Ser Lys Gly Cys Thr Asp Pro Ser Asn Gly Leu Phe Trp Ala Ser Val
                    195                 200                 205
    Ser Glu His Ser Glu Leu Gln Ile Thr Thr Ile Pro Leu Pro Pro His
        210                 215                 220
    Arg Gln Leu Ser Arg Leu Pro Gln Pro Phe Phe Asp Lys Asn Val Lys
    225                 230                 235                 240
    Gln Lys Ile Val Ile Pro Phe Val Leu Ala Gln Thr Phe Asp Pro Glu
                    245                 250                 255
    Val Leu Lys Ala Thr Gly Ile Leu Ala Ser Trp Phe Gly Gln Gln Thr
                    260                 265                 270
    Asp Tyr Arg Gly Val Thr Phe Pro Val Phe Ser Thr Ile Pro Gln Thr
                    275                 280                 285
    Gly Asn Ala Val Val Val Gly Val Ala Asp Glu Leu Pro Ser Ala Leu
        290                 295                 300
    Gly Arg Gln Ala Val Ser Gly Pro Thr Leu Met Glu Val Ala Asn Pro
    305                 310                 315                 320
    Ser Asp Pro Asn Gly Thr Ile Leu Leu Val Thr Gly Arg Asp Arg Asp
                    325                 330                 335
    Glu Val Ile Thr Ala Ser Lys Gly Ile Gly Phe Gly Ser Ser Thr Leu
                    340                 345                 350
    Pro Thr Ala Asn Arg Met Asp Val Ala Pro Ile Glu Val Gly Ala Arg
                    355                 360                 365
    Val Ala Asn Asp Ala Pro Ser Phe Ile Pro Thr Asn Arg Pro Val Arg
        370                 375                 380
    Leu Gly Glu Leu Val Pro Asp Ser Ala Leu Gln Ala Glu Gly Tyr Ala
    385                 390                 395                 400
    Pro Gly Ala Leu Ala Val Pro Phe Arg Val Ser Pro Asp Leu Tyr Thr
                    405                 410                 415
    Trp Arg Asp Arg Pro Asn Lys Leu Asn Val Arg Phe Arg Ala Pro Pro
                    420                 425                 430
    Gly Pro Ile Val Asp Val Ser Arg Ser Ser Leu Asn Val Gly Ile Asn
                    435                 440                 445
    Asp Thr Tyr Leu Glu Ala Tyr Pro Leu Arg Glu Pro Asp Ser Pro Leu
        450                 455                 460
    Asp Gln Leu Leu His Gly Val Gly Leu Gly His Arg Asn Asn Asp Ser
    465                 470                 475                 480
    Val Gln Gln His Thr Met Pro Ile Pro Thr Tyr Arg Val Phe Gly Gln
                    485                 490                 495
```

-continued

Asn Gln Leu Leu Phe Tyr Phe Glu Met Ala Ala Met Val Glu Pro Gly
            500                 505                 510

Cys Lys Pro Gly Pro Ser Thr Phe His Met Gly Ile Asp Pro Asn Ser
            515                 520                 525

Thr Ile Asp Leu Ser Asn Ser Tyr His Ile Thr Gln Met Pro Asn Leu
            530                 535                 540

Ala Phe Met Ala Ser Ala Gly Phe Pro Phe Thr Thr Tyr Ala Asp Leu
545                 550                 555                 560

Ser Arg Ser Ala Val Val Leu Pro Glu His Pro Asn Gly Met Ile Val
                565                 570                 575

Ser Ala Tyr Leu Asp Leu Met Gly Phe Met Gly Ala Thr Thr Trp Tyr
            580                 585                 590

Pro Val Ser Gly Val Asp Val Ser Ser Asp His Val Asn Asp Val
            595                 600                 605

Ala Asp Arg Asn Leu Ile Val Leu Ser Thr Leu Ala Asn Ser Gly Asp
610                 615                 620

Val Ser Gln Leu Leu Ser Asn Ser Ala Tyr Gln Ile Ser Asp Gly Arg
625                 630                 635                 640

Leu His Met Ala Leu Arg Ser Thr Leu Ser Gly Val Trp Asn Leu Phe
                645                 650                 655

Gln Asp Pro Met Ser Ala Ile Asn Ser Thr Ala Pro Thr Asp Val Glu
            660                 665                 670

Ser Thr Leu Thr Gly Gly Val Ala Ala Met Val Glu Ala Glu Ser Pro
            675                 680                 685

Leu Ala Ser Gly Arg Thr Val Leu Ala Leu Ser Gly Asp Gly Gln
690                 695                 700

Gly Leu Asn Asn Leu Val Gln Ile Leu Ala Gln Arg Lys Asn Gln Ala
705                 710                 715                 720

Lys Ile Gln Gly Asp Leu Val Leu Ala His Gly Asp Asp Leu Thr Ser
                725                 730                 735

Tyr Arg Ser Ser Pro Leu Tyr Thr Val Gly Thr Val Pro Leu Trp Leu
            740                 745                 750

Lys Pro Asp Trp Tyr Met His Asn His Pro Ser Arg Val Val Val Val
            755                 760                 765

Gly Leu Phe Gly Cys Leu Leu Val Ala Val Leu Met Arg Ala Leu
770                 775                 780

Thr Lys His Ala Leu Arg Arg Arg Glu Leu Gln Glu Glu Arg Gln
785                 790                 795                 800

Arg Thr

<210> SEQ ID NO: 5
<211> LENGTH: 1326
<212> TYPE: PRT
<213> ORGANISM: Acetobacter xylinum
<220> FEATURE:
<223> OTHER INFORMATION: n at positions 15741 and 15767 may be a, g, t,
      or c

<400> SEQUENCE: 5

Met Asn Arg Arg Tyr Ala Leu Ser Leu Ser Gly Ala Leu Leu Ala Ser
 1               5                  10                  15

Ser Cys Met Thr Val Leu Val Ala Val Pro Val Ala Arg Ala Gln Gln
            20                  25                  30

Ala Ser Thr Ala Val Thr Ser Thr Ala Ala Ser Pro Ala Ala Ala Pro
            35                  40                  45

```
Arg Gln Ile Leu Leu Gln Gln Ala Arg Phe Trp Leu Gln Gln Gln
 50                      55                      60

Tyr Asp Asn Ala Arg Gln Ala Leu Gln Asn Ala Gln Arg Ile Ala Pro
 65                      70                      75                  80

Asp Ala Pro Asp Val Leu Glu Val Glu Gly Glu Tyr Gln Ala Ala Val
                     85                      90                      95

Gly Asn Arg Glu Ala Ala Ala Asp Thr Leu Arg His Leu Gln Gln Val
                100                     105                     110

Ala Pro Ala Ser Thr Ala Val Ser Asn Leu Ser Asp Leu Leu Ser Glu
            115                     120                     125

Arg Ala Ile Ser Gln Ser Asp Leu Ser Gln Ile Arg Ser Leu Ala Gly
        130                     135                     140

Ser Gly Gln Asn Ala Gln Ala Val Ala Gly Tyr Gln Lys Leu Phe His
145                     150                     155                     160

Gly Gly Lys Pro Pro Arg Ser Leu Ala Val Glu Tyr Tyr Gln Thr Met
                165                     170                     175

Ala Gly Val Pro Thr Gln Trp Asp Gln Ala Arg Ala Gly Leu Ala Gly
            180                     185                     190

Ile Val Ala Ser Asn Pro Gln Asn Tyr Arg Ala Gln Leu Ala Phe Ala
        195                     200                     205

Gln Ala Leu Thr Tyr Asn Thr Ser Thr Arg Met Glu Gly Leu Thr Arg
210                     215                     220

Leu Lys Asp Leu Gln Ser Phe Gln Ser Gln Ala Pro Val Glu Ala Ala
225                     230                     235                     240

Ala Ala Thr Gln Ser Tyr Arg Gln Thr Leu Ser Trp Leu Pro Val Asn
                245                     250                     255

Pro Asp Thr Gln Pro Leu Met Glu Gln Trp Leu Ser Ala His Pro Asn
            260                     265                     270

Asp Ala Ala Leu Arg Glu His Met Leu His Pro Pro Gly Gly Pro Pro
        275                     280                     285

Asp Lys Ala Gly Leu Ala Arg Gln Ala Gly Tyr Gln Gln Leu Asn Ala
        290                     295                     300

Gly Arg Leu Ser Ala Ala Glu Gln Ser Phe Gln Ser Ala Leu Gln Ile
305                     310                     315                     320

Asn Ser His Asp Ala Asp Ser Leu Gly Gly Met Gly Leu Val Ser Met
                325                     330                     335

Arg Gln Gly Asp Thr Ala Glu Ala His Pro Tyr Phe Glu Glu Ala Met
            340                     345                     350

Ala Ala Asp Pro Lys Thr Ala Asp Arg Trp Arg Pro Ala Leu Ala Gly
        355                     360                     365

Met Ala Val Ser Gly Asp Tyr Ala Ala Val Arg Gln Leu Ile Ala Ala
        370                     375                     380

His Gln Tyr Thr Glu Ala Lys Gln Lys Leu Ala Thr Leu Ala Arg Gln
385                     390                     395                     400

Pro Gly Gln Tyr Thr Gly Ala Thr Leu Met Leu Ala Asp Leu Gln Arg
                405                     410                     415

Ser Thr Gly Gln Val Ala Ala Glu Gln Glu Tyr Arg Gly Ile Leu
            420                     425                     430

Ser Arg Glu Pro Asn Asn Gln Leu Ala Leu Met Gly Leu Ala Arg Val
        435                     440                     445

Asp Met Ala Gln Gly Asn Thr Ala Glu Ala Arg Gln Leu Leu Ser Arg
450                     455                     460
```

-continued

```
Val Ser Pro Gln Tyr Ala Ser Gln Val Gly Glu Ile Glu Val Ser Gly
465                 470                 475                 480

Leu Met Ala Ala Ser Gln Thr Ser Asp Ser Ala Arg Lys Val Ser
            485                 490                 495

Ile Leu Arg Glu Ala Met Ala Gln Ala Pro Arg Asp Pro Trp Val Arg
                500                 505                 510

Ile Asn Leu Ala Asn Ala Leu Gln Gln Gly Asp Val Ala Glu Ala
            515                 520                 525

Gly Arg Val Met Gln Pro Ile Leu Ala Asn Pro Val Thr Ala Gln Asp
530                 535                 540

Arg Gln Ala Gly Ile Leu Tyr Thr Tyr Gly Ser Gly Asn Asp Ala Met
545                 550                 555                 560

Thr Arg Gln Leu Leu Ala Gly Leu Ser Pro Ala Asp Tyr Ser Pro Ala
                565                 570                 575

Ile Arg Ser Ile Ala Glu Glu Met Glu Ile Lys Gln Asp Leu Ala Ser
            580                 585                 590

Arg Leu Ser Met Val Ser Asn Pro Val Pro Leu Ile Arg Glu Ala Leu
        595                 600                 605

Ser Gln Pro Asp Pro Thr Gly Ala Arg Gly Val Ala Val Ala Asp Leu
    610                 615                 620

Phe Arg Gln Arg Gly Asp Met Val His Ala Arg Met Ala Leu Arg Ile
625                 630                 635                 640

Ala Ser Thr Arg Thr Ile Asp Leu Ser Pro Asp Gln Arg Leu Ser Tyr
                645                 650                 655

Ala Thr Glu Tyr Met Lys Ile Ser Asn Pro Val Ala Ala Arg Leu
            660                 665                 670

Leu Ala Pro Leu Gly Asp Gly Thr Gly Ser Gly Ala Gly Asn Ala Leu
        675                 680                 685

Leu Pro Glu Gln Met Gln Thr Leu Gln Gln Leu Arg Met Gly Ile Ser
    690                 695                 700

Val Ala Gln Ser Asp Leu Leu Asn Gln Arg Gly Asp Gln Ala Gln Ala
705                 710                 715                 720

Tyr Asp His Leu Ala Pro Ala Leu Gln Ala Asp Pro Glu Ala Thr Ser
                725                 730                 735

Pro Lys Leu Ala Leu Ala Arg Leu Tyr Asn Gly His Gly Lys Pro Gly
            740                 745                 750

Lys Ala Leu Glu Ile Asp Leu Ala Val Leu Arg His Asn Pro Gln Asp
        755                 760                 765

Leu Asp Ala Arg Gln Ala Ala Val Gln Ala Val Asn Ser Asn His
    770                 775                 780

Asn Ser Leu Ala Thr Arg Leu Ala Met Asp Gly Val Gln Glu Ser Pro
785                 790                 795                 800

Met Asp Ala Arg Ala Trp Leu Ala Met Ala Val Ala Asp Gln Ala Asp
                805                 810                 815

Gly His Gly Gln Arg Thr Ile Glu Asp Leu Arg Arg Ala Tyr Asp Leu
            820                 825                 830

Arg Leu Gln Gln Val Glu Gly Thr Arg Ala Ala Ser Gly Pro Val Gly
        835                 840                 845

Ala His Glu Glu Ala Leu Ala Pro Pro Ser Thr Asn Pro Phe Gln Ser
    850                 855                 860

Arg Gly Tyr Gly His Gln Val Glu Leu Gly Ala Pro Val Thr Gly Gly
865                 870                 875                 880

Ser Tyr Ser Ala Glu Ala Ala Ser Pro Asp Thr Ser Asp Gln Met Leu
```

-continued

```
                885                 890                 895
Ser Ser Ile Ala Gly Gln Ile His Thr Leu Arg Glu Asn Leu Ala Pro
            900                 905                 910

Ser Ile Asp Gly Gly Leu Gly Phe Arg Ser Arg Ser Gly Glu His Gly
            915                 920                 925

Met Gly Arg Leu Thr Glu Ala Asn Ile Pro Ile Val Gly Arg Leu Pro
            930                 935                 940

Leu Gln Ala Gly Ala Ser Ala Leu Thr Phe Ser Ile Thr Pro Thr Met
945                 950                 955                 960

Ile Trp Ser Gly Gln Leu Asn Thr Gly Ser Val Tyr Asp Val Pro Arg
            965                 970                 975

Tyr Gly Thr Phe Met Ala Thr Gln Ala Ala Asn Gln Cys Ala Gly His
            980                 985                 990

Ser Ser Cys Gly Gly Leu Asp Phe Leu Ser Ala Asn His Thr Gln Arg
            995                 1000                1005

Ile Ala Ala Gly Ala Gly Glu Ala Gly Phe Ala Pro Asp Val Gln Phe
        1010                1015                1020

Gly Asn Ser Trp Val Arg Ala Asp Val Cys Ala Ser Pro Ile Gly Phe
1025                1030                1035                1040

Pro Ile Thr Asn Val Leu Gly Gly Val Glu Phe Ser Pro Arg Val Gly
            1045                1050                1055

Pro Val Thr Phe Arg Val Ser Ala Glu Arg Arg Ser Ile Thr Asn Ser
            1060                1065                1070

Val Leu Ser Tyr Gly Gly Leu Arg Asp Pro Asn Tyr Asn Ser Glu Val
            1075                1080                1085

Gly Arg Tyr Ala Arg Gln Val Tyr Gly His Asp Leu Thr Lys Gln Trp
        1090                1095                1100

Gly Ser Glu Trp Gly Gly Val Val Thr Asn His Phe His Gly Gln Val
1105                1110                1115                1120

Glu Ala Thr Leu Gly Asn Thr Ile Leu Tyr Gly Gly Gly Tyr Ala
            1125                1130                1135

Ile Gln Thr Gly Lys Asn Val Gln Arg Asn Ser Glu Arg Glu Ala Gly
        1140                1145                1150

Ile Gly Ala Asn Thr Leu Val Trp His Asn Ala Asn Met Leu Val Arg
        1155                1160                1165

Ile Gly Val Ser Leu Thr Tyr Phe Gly Tyr Ala His Asn Glu Asp Phe
1170                1175                1180

Tyr Thr Tyr Gly Gln Gly Gly Tyr Phe Ser Pro Gln Ser Tyr Tyr Ala
1185                1190                1195                1200

Ala Thr Val Pro Val Arg Tyr Ala Gly Gln His Lys Arg Leu Asp Trp
        1205                1210                1215

Asp Val Thr Gly Ser Val Gly Tyr Gln Val Phe His Glu His Ala Ala
        1220                1225                1230

Pro Phe Phe Pro Thr Ser Ser Leu Leu Gln Ser Gly Ala Asn Tyr Val
        1235                1240                1245

Ala Ser Asn Phe Val Gln Asn Ala Leu Pro Thr Asp Tyr Leu Ser Gln
        1250                1255                1260

Glu Thr Val Asn Ser Ala Tyr Tyr Pro Gly Asp Ser Ile Ala Gly Leu
1265                1270                1275                1280

Thr Gly Gly Phe Asn Ala Arg Val Gly Tyr Arg Phe Thr Arg Asn Val
            1285                1290                1295

Arg Leu Asp Leu Ser Gly Arg Tyr Gln Lys Ala Gly Asn Trp Thr Glu
        1300                1305                1310
```

-continued

```
Ser Gly Ala Met Ile Ser Ala His Tyr Leu Ile Met Asp Gln
        1315                1320                1325

<210> SEQ ID NO: 6
<211> LENGTH: 156
<212> TYPE: PRT
<213> ORGANISM: Acetobacter xylinum
<220> FEATURE:
<223> OTHER INFORMATION: n at positions 15741 and 15767 may be a, g, t,
      or c

<400> SEQUENCE: 6

Met Thr Thr Leu Asn Ala Lys Pro Asp Phe Ser Leu Phe Leu Gln Ala
  1               5                  10                  15

Leu Ser Trp Glu Ile Asp Asp Gln Ala Gly Ile Glu Val Arg Asn Asp
             20                  25                  30

Leu Leu Arg Glu Val Gly Arg Gly Met Ala Gly Arg Phe Gln Pro Pro
         35                  40                  45

Leu Cys Asn Thr Ile His Gln Leu Gln Ile Glu Leu Asn Ala Leu Leu
     50                  55                  60

Ala Met Ile Asn Trp Gly Tyr Val Lys Leu Asp Leu Leu Ala Glu Glu
 65                  70                  75                  80

Gln Ala Met Arg Ile Val His Glu Asp Leu Pro Gln Val Gly Ser Ala
                 85                  90                  95

Gly Glu Pro Ala Gly Thr Trp Leu Ala Pro Val Leu Glu Gly Leu Tyr
            100                 105                 110

Gly Arg Trp Ile Thr Ser Gln Pro Gly Ala Phe Gly Asp Tyr Val Val
        115                 120                 125

Thr Arg Asp Ile Asp Ala Glu Asp Leu Asn Ser Val Pro Ala Gln Thr
    130                 135                 140

Val Ile Leu Tyr Met Arg Thr Arg Ser Ala Ala Thr
145                 150                 155

<210> SEQ ID NO: 7
<211> LENGTH: 735
<212> TYPE: PRT
<213> ORGANISM: Acetobacter xylinum
<220> FEATURE:
<223> OTHER INFORMATION: n at positions 15741 and 15767 may be a, g, t,
      or c

<400> SEQUENCE: 7

Met Arg Leu Ser Arg Lys Ile Phe Leu Leu Ser Ala Val Ala Cys Gly
  1               5                  10                  15

Met Ala Leu Ala Gln Ala Pro Phe Ala Arg His Ala His Asp Gly
             20                  25                  30

Gly Gly Asp Gln Ala Asp Ala Arg Ala Arg Gln Val Leu Ala Ser Met
         35                  40                  45

Ser Leu Glu Asp Lys Met Ser Leu Leu Phe Ser Val Asp Gly Gly Gly
     50                  55                  60

Phe Asn Gly Ser Val Ala Pro Pro Gly Gly Leu Gly Ser Ala Ala Tyr
 65                  70                  75                  80

Leu Arg Ala Pro Gln Gly Ser Gly Leu Pro Asp Leu Gln Ile Ser Asp
                 85                  90                  95

Ala Gly Leu Gly Val Arg Asn Pro Ala His Ile Arg Arg Asn Gly Glu
            100                 105                 110

Ala Val Ser Leu Pro Ser Gly Gln Ser Thr Ala Ser Thr Trp Asp Met
        115                 120                 125
```

```
Asp Met Ala Arg Gln Ala Gly Val Met Ile Gly Arg Glu Ala Trp Gln
    130                 135                 140

Ser Gly Phe Asn Ile Leu Leu Gly Gly Ala Asp Leu Thr Arg Asp
145                 150                 155                 160

Pro Arg Gly Gly Arg Asn Phe Glu Tyr Ala Gly Glu Asp Pro Leu Gln
                165                 170                 175

Thr Gly Arg Met Val Gly Ser Thr Ile Ala Gly Val Gln Ser Gln His
            180                 185                 190

Val Ile Ser Thr Leu Lys His Tyr Ala Met Asn Asp Leu Glu Thr Ser
        195                 200                 205

Arg Met Thr Met Ser Ala Asp Ile Asp Pro Val Ala Met Arg Glu Ser
    210                 215                 220

Asp Leu Leu Gly Phe Glu Ile Ala Leu Glu Thr Gly His Pro Gly Ala
225                 230                 235                 240

Val Met Cys Ser Tyr Asn Arg Val Asn Asp Leu Tyr Ala Cys Glu Asn
                245                 250                 255

Pro Tyr Leu Leu Asn Lys Thr Leu Lys Gln Asp Trp His Tyr Pro Gly
                260                 265                 270

Phe Val Met Ser Asp Trp Gly Ala Thr His Ser Ser Ala Arg Ala Ala
            275                 280                 285

Leu Ala Gly Leu Asp Gln Glu Ser Ala Gly Asp His Thr Asp Ala Arg
    290                 295                 300

Pro Tyr Phe Arg Thr Leu Leu Ala Ala Asp Val Lys Ala Gly Arg Val
305                 310                 315                 320

Pro Glu Ala Arg Ile Asn Asp Met Ala Glu Arg Val Val Arg Ala Leu
                325                 330                 335

Phe Ala Ala Gly Leu Val Asp His Pro Ala Gln Arg Gly Pro Leu Asp
                340                 345                 350

Val Val Thr Asp Thr Leu Val Ala Gln Lys Asp Glu Glu Glu Gly Ala
            355                 360                 365

Val Leu Leu Arg Asn Gln Gly Asn Ile Leu Pro Leu Ser Pro Thr Ala
    370                 375                 380

Arg Ile Ala Val Ile Gly Gly His Ala Asp Ala Gly Val Ile Ser Gly
385                 390                 395                 400

Gly Gly Ser Ser Gln Val Asp Pro Ile Gly Gly Glu Ala Val Lys Gly
                405                 410                 415

Pro Gly Lys Lys Glu Trp Pro Gly Asp Pro Val Tyr Phe Pro Ser Ser
                420                 425                 430

Pro Leu Lys Ala Met Gln Ala Glu Ala Pro Gly Ala Arg Ile Thr Tyr
                435                 440                 445

Asp Pro Gly Thr Ser Ile Ala Ser Ala Val Arg Ala Arg Ala Ala
    450                 455                 460

Asp Val Val Val Tyr Ala Thr Gln Phe Thr Phe Glu Gly Met Asp
465                 470                 475                 480

Ala Pro Ser Met His Leu Asp Asp Asn Ala Asp Ala Leu Ile Thr Ala
                485                 490                 495

Val Ala Ala Ala Asn Pro Arg Thr Val Val Met Glu Thr Gly Asp
        500                 505                 510

Pro Val Leu Met Pro Trp Asn Ser Ser Val Ala Gly Val Leu Glu Ala
            515                 520                 525

Trp Phe Pro Gly Ser Gly Gly Pro Ala Ile Ala Arg Leu Leu Phe
    530                 535                 540
```

```
Gly Lys Val Ala Pro Ser Gly His Leu Thr Met Thr Phe Pro Gln Ala
545                 550                 555                 560

Glu Ser Gln Leu Ala His Pro Asp Ile Ala Gly Val Thr Ala Asp Asn
            565                 570                 575

Val Phe Glu Met Gln Phe His Thr Asp Gln Glu Leu Val Tyr Asp Glu
        580                 585                 590

Gly Ser Asp Val Gly Tyr Arg Trp Phe Asp Arg Asn His Phe Lys Pro
    595                 600                 605

Leu Tyr Pro Phe Gly Tyr Gly Leu Thr Tyr Thr Thr Phe Ser Thr Asp
        610                 615                 620

Gly Leu Lys Val Thr Glu Arg His Gly Gln Val Thr Ala Thr Phe Asn
625                 630                 635                 640

Val His Asn Thr Gly Thr Arg Ala Gly Val Asp Val Pro Gln Val Tyr
                645                 650                 655

Val Gly Leu Pro Asp Gly Gly Ala Arg Arg Leu Ala Gly Trp Gln Arg
            660                 665                 670

Ile Ser Leu Ala Pro Gly Glu Ser Arg Gln Val Ser Val Gln Leu Glu
        675                 680                 685

Pro Arg Leu Leu Ala His Phe Asp Gly Lys His Asp Arg Trp Ser Val
690                 695                 700

Pro Ser Gly Thr Phe Arg Val Trp Leu Ala Ser Cys Ala Thr Asp Asp
705                 710                 715                 720

Ser Gln Gln Thr Thr Met His Leu His Gly Arg Thr Met Ala Pro
                725                 730                 735

<210> SEQ ID NO: 8
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
accgaatgcg tctgacggtt                                              20

<210> SEQ ID NO: 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
tgatgatggt tacgcgcacc                                              20

<210> SEQ ID NO: 10
<211> LENGTH: 16836
<212> TYPE: DNA
<213> ORGANISM: Acetobacter xylinum
<220> FEATURE:
<221> NAME/KEY: CDS
<222> LOCATION: (1891)..(2922)
<220> FEATURE:
<223> OTHER INFORMATION: Nucleotide sequence is the same as SEQ ID NO: 1
<220> FEATURE:
<223> OTHER INFORMATION: n at positions 15741 and 15767 may be a, g, c,
      or t

<400> SEQUENCE: 10
ggatccactg gcgcggcgca tcacggcgcg gctggtgctg ggcacccct gaacacaaat    60
```

-continued

```
gcggggcgtg cgtgattctt tgcttgcatg cccccgcaac atcgcctaga aggcggctac    120
cggccttttg tcccgttcgt ctagaggcct aggacactgc cctctcacgg cggcaacagg    180
ggttcgaatc ccctacggga cgccagccag ttctggctga ataaaagact gactgatgaa    240
aacccgccgc aaggcgggtt tttcgtatgt acttcgtttt tttataaata tctttgacca    300
gaagcctgtc tgcgctatgg caaggcaact ttatttatat taatatataa taaaagcatc    360
ttatatactg cggtctgccc gtctgctaaa aagcattgat ccagatcaat cgcgtctgaa    420
atttaaaaat attttccgtc ttttaatttt gcaaaagatg acaccagtag tgaacggcga    480
tcgtttgcca tatttctctt ctttaatttc cttaggaatt atcaacggtt tttacagagg    540
gccatttgcc cctgcgtgac aaaaatgcaa cttttcttc cctgtagcca gttgtggcgc    600
tggtggcggt ttcgccgctg gggggagaga cgttatgctc cttttcagta ataaagtctg    660
tcccggaatg gtcgccttcg acttgcagga tggaggagtt tccgattaag gcgtcatggc    720
gtggcagggt attgagggcg catcaggcgt tcggccagac actggcgtgg gttcagactt    780
cttgagggtg tggtggtaga tgctgttgga ttttatgaag ctgcaaaaac atgtatccgg    840
gatggggcgt cgctcctttc tgtccgtcat ggctgtggct ggcagctttc ccatgctttc    900
ctccggcgct gaagctgatg atgccattgg catcaacccg cagatcgccc agcagtgggc    960
cattttccgg gacaagtatt ttcatcccaa cgggcgcatc atcgatacgg gcaatagcgg   1020
cgaatcccac agcgagggc agggctacgg catgctcttt tccgctgcgg cgggcgacca   1080
ggcggcgttc gaggtaatct gggtctgggc gcgcaccaac ctgcagcaca aggatgacgc   1140
cctgttctcc tggcgttacc ttgacgggca aaaccgccc gtggccgaca gaacaacgc    1200 aaccgacggg gacctgctca ttgccctcgc cctggcttgg gccggcaagc gatggaagcg   1260
cgccgactat attcaggacg ccatgaacat ctatggcgac gtgctgaaac tcatgacgaa   1320
gtccgtcggc ccctacacgg tgctgctgcc gggcgctgtc gggtttctca ccaaggatac   1380
ggtcacgctg aacctgtcct attacgtcat gccctccctc atgcaggcct ttgcgctcac   1440
gggtgatgcg aagtggacaa aggtgatggg cgacgggctg cagatcatcg ccaagggacg   1500
attcggtgaa tggaagctcc cgccggactg gctgtcgatc aacctgcata ccaacgcctt   1560
ctccattgcc aagggctggc cgccgcgctt ctcgtatgat gcgattcgcg tgccgctcta   1620
cttgtcttgg gcgcatatgc tgaccccgga actgctggcg gatttcagcc ggttctggaa   1680
ccattatggc gcatccgccc tgccgggctg ggttgatctg accaacggcg cgcgttcgcc   1740
ctataatgcg ccgccgggct atctggcggt ggcgtcatgc acgggcctgg cctcggcggg   1800
tgaactgccc acgtcgatc atgcgcccga ctactattcg gccgcgttga cgatgctggc   1860
ctatatcgcc cggaaccagg gagatgggat gtg agc aca cct gaa aag gaa gca   1914
                                 Val Ser Thr Pro Glu Lys Glu Ala
                                  1               5 gga acg cag gtg aat atc gac aac cag cag gat gtc gac cgt atg ctg    1962
Gly Thr Gln Val Asn Ile Asp Asn Gln Gln Asp Val Asp Arg Met Leu
         10              15                  20 acg gat ggc tac ggt atc agc agt gca ggt ttt cac tac cgc cct ttc    2010
Thr Asp Gly Tyr Gly Ile Ser Ser Ala Gly Phe His Tyr Arg Pro Phe
 25              30                  35                  40 aag cag aag cgc ccg ccc agg cca gaa gtc agg cac gac gag tct ggc    2058
Lys Gln Lys Arg Pro Pro Arg Pro Glu Val Arg His Asp Glu Ser Gly
             45                  50                  55 gca gag cag gcc gca gca gcc gag cac gct cct gcc gct gaa gaa gca    2106
Ala Glu Gln Ala Ala Ala Ala Glu His Ala Pro Ala Ala Glu Glu Ala
```

```
                       60                  65                  70
tcg cag cat ttc gtt tct tcc tac gat gat acc tat tcc acc ccg gca    2154
Ser Gln His Phe Val Ser Ser Tyr Asp Asp Thr Tyr Ser Thr Pro Ala
            75                  80                  85 gcg cct gag gct gcg cct gtt gag gca gca gaa cag ccg cag cac tac    2202
Ala Pro Glu Ala Ala Pro Val Glu Ala Ala Glu Gln Pro Gln His Tyr
        90                  95                 100 ggg gaa aca gcc tac acg cct gcc gcg cat gat gcc tat gcc gca cag    2250
Gly Glu Thr Ala Tyr Thr Pro Ala Ala His Asp Ala Tyr Ala Ala Gln
105                 110                 115                 120 ccg gag ccg gaa cag gcc gcg ccc gag cct tat gtt gcg cat gac gat    2298
Pro Glu Pro Glu Gln Ala Ala Pro Glu Pro Tyr Val Ala His Asp Asp
                125                 130                 135 acg ccc gca gcc gaa ccc gag acc tat gcc gcc acg cac gcc gaa acc    2346
Thr Pro Ala Ala Glu Pro Glu Thr Tyr Ala Ala Thr His Ala Glu Thr
            140                 145                 150 gta acg gtt ccg gaa tat gcg gcc gcc cct cag cca gtt gcg acc ccc    2394
Val Thr Val Pro Glu Tyr Ala Ala Ala Pro Gln Pro Val Ala Thr Pro
        155                 160                 165 gtg ccg ccg cag ccc gcg ccc gtg gcc ccg gtt gtt gct gcc gtg gcg    2442
Val Pro Pro Gln Pro Ala Pro Val Ala Pro Val Val Ala Ala Val Ala
170                 175                 180 cag ccg gtc agg cag gag cgg ccc tca ttg tcg cca gtg acg ccc ccc    2490
Gln Pro Val Arg Gln Glu Arg Pro Ser Leu Ser Pro Val Thr Pro Pro
185                 190                 195                 200 aaa cct gcg gtg tct tcc ttc atg gcg ccc cgt cct gcc ccg gct ttt    2538
Lys Pro Ala Val Ser Ser Phe Met Ala Pro Arg Pro Ala Pro Ala Phe
            205                 210                 215 ggc tcg gct tca gcc acg ccc ccc atc gca gca gag gac tgg gcc ccc    2586
Gly Ser Ala Ser Ala Thr Pro Pro Ile Ala Ala Glu Asp Trp Ala Pro
        220                 225                 230 gtg ccc aag gcc cag cag cag cgt ggg cag cgt ttg aca ggg cca ggc    2634
Val Pro Lys Ala Gln Gln Gln Arg Gly Gln Arg Leu Thr Gly Pro Gly
    235                 240                 245 ttc ttt ttt ggt gcg gga agt gag cgg gcg ccc gca gca agg ctg ttc    2682
Phe Phe Phe Gly Ala Gly Ser Glu Arg Ala Pro Ala Ala Arg Leu Phe
250                 255                 260 cag tcg gca ccg gtg tcc cgg cct gtt tca aaa cct gtt tcc aag gtg    2730
Gln Ser Ala Pro Val Ser Arg Pro Val Ser Lys Pro Val Ser Lys Val
265                 270                 275                 280 acc aca atg acc aaa gtt gac aag agt tcc ccg aat gac agt cag gca    2778
Thr Thr Met Thr Lys Val Asp Lys Ser Ser Pro Asn Asp Ser Gln Ala
            285                 290                 295 ggc cgc cct gca ccg acc gac aat tct ccg acc ctg acc gaa gtg ttc    2826
Gly Arg Pro Ala Pro Thr Asp Asn Ser Pro Thr Leu Thr Glu Val Phe
        300                 305                 310 atg acc ctt ggc ggt cgg gcc acg gat cgg ctg gtg ccc aag ccc agc    2874
Met Thr Leu Gly Gly Arg Ala Thr Asp Arg Leu Val Pro Lys Pro Ser
    315                 320                 325 ctg cgt gat gcc ctg ttg cgc aag cgt gaa ggc acg aac ggc gaa tcc    2922
Leu Arg Asp Ala Leu Leu Arg Lys Arg Glu Gly Thr Asn Gly Glu Ser
330                 335                 340 tgacaccgtg ccgggagcag tctgctcccg gcctgccaaa ggaaagaagg gggaaggttt    2982 tcccatccc gcacaagcgg cgggccgaaa ggcgacatga cggaccgaat gcgtctgacg    3042
gttttctttt gaatatatct acctgtttta tcagtattta ttatcggacg agctattgat    3102
gtcagaggtt cagtcgccag tacccacgga gagtaggcta ggccgcatct ccaacaagat    3162
actgtcactg cgtggggcca gctatatagt tggagcgctg gggctttgtg cacttattgc    3222
```

-continued

```
cgcgaccacg gttacgctga acaataatga gcagctaatt gtggcagctg tatgtgttgt    3282
catctttttt gttgtcgggc gtggcaagag ccggcgcacc cagattttc tcgaggtgct     3342
ctccgcgctg gtttccctgc gttacctgac atggcgcctg accgaaacgc tcgacttcaa    3402
tacatggatt cagggcatac tgggcgtaat cctgctcatg gccgagctgt atgccctgta    3462
catgctgttt ctcagctatt tccagacaat ccagccgctt catcgtgcgc cgctgccct     3522
gcctgacaat gttgacgact ggccgactgt cgatatcttc atcccgacct atgatgagca    3582
gctgagcatc gtgcgcctga ccgtgctggg cgcgctcggc atcgactggc cgcccgataa    3642
agtgaatgtc tatatccttg atgacggtgt gcggcccgaa ttcgagcagt tcgccaagga    3702
ttgcggcgcc ctgtatatcg ggcgtgtcga cgtcgacagc gcgcacgcca aggcgggtaa    3762
cctcaaccac gccattaagc ggacttccgg cgattacatc ctcatcctgg attgtgacca    3822
tattccgaca cgcgcgttcc tgcagatcgc catggggtgg atggtcgctg accgcaagat    3882
cgccctgatg cagacgccgc atcacttcta ctctcccgat ccgttccagc gtaacctggc    3942
cgtgggctac cgcaccccgc cggaaggcaa cctgttctac ggcgtcatcc aggatggcaa    4002
cgacttctgg gatgccacct tcttctgcgg ctcatgcgcc atcctgcggc gtgaggccat    4062
tgaatcgatc ggcggctttg cggttgaaac cgtgacggaa gatgcccata ccgccctgcg    4122
catgcagcgc cgcggctggt ccaccgctta cctgcgcatt cccgttgcca gtggtctggc    4182
caccgagcga ctgaccaccc atatcggcca gcgcatgcgc tgggcgcgcg catgatcca    4242
gatcttccgc gtggataacc cgatgctcgg gcgcggcctg aagttgggcc agcggctttg    4302
ctatctttcg gccatgacgt cgttcttctt cgccattccg cgcgttatct tccttgcctc    4362
gccgctggcg ttcctgtttg cgggccagaa catcatcgcc gccgcgccac tggccgtggc    4422
ggcctatgcc ctcccgcaca tgttccactc cattgcaacc gccgcaagg tgaacaaggg    4482
ctggcgctat tcgttctgga gtgaggtgta cgaaaccacc atggcgctgt tcctggtgcg    4542
cgtgaccatc gtcaccctgc tgttcccctc caagggcaaa ttcaacgtga cggaaaaggg    4602
cggcgtgctt gaggaggaag agttcgatct tggggcgacc taccccaaca tcattttcgc    4662
caccatcatg atgggtggcc tgctgatcgg tctgttcgag ttgatcgtgc gtttcaatca    4722
gctcgatgtc attgccagga acgcttatct cctgaactgc gcctgggcgc tgatcagtct    4782
catcatcctt ttcgctgcca ttgccgtggg gcgcgagacc aagcaggtcc gttacaacca    4842
tcgtgtcgaa gcgcatatcc cggtaacggt ttacgatgcg cctgccgaag ggcagcccca    4902
tacctattat aatgcgacgc acggcatgac ccaggatgtt ccatgggtg gtgttgccgt     4962
gcacatcccc ttgcccgatg tcaccacggg gcctgtcaag aaacgtatcc atgccgtgct    5022
tgatggcgag gaaatccata ttcccgccac catgctgcgc tgcacgaatg gcaaggccgt    5082
gttcacatgg gacaataatg accttgatac ggaacgcgat attgtccgct tcgtgttcgg    5142
gcgggctgat gcctggctgc aatggaacaa ttatgaggat gacagaccgc tacgcagcct    5202
gtggagcctg ctgctcagca ttaaggcgct gttccgcaaa aaaggcaaaa taatggccaa    5262
tagtcgtcca aaaaagaaac cacttgcact accggttgag cgcagggagc ccacaaccat    5322
ccacagtgga cagactcaag aaggaaagat cagccgtgcg gcctcgtgat atgaaaatgg    5382
tgtccctgat cgcgctgctg gtctttgcaa cgggggcaca ggctgcgcct gttgcttcca    5442
aggcgccagc tccgcagccc gcaggttcag acctgccacc tctccctgcc gcaccgccgc    5502
aggctgctcc gcccgcagcc gcgagtgccg ccccgcccgc cacaaccccg gcggcggatg    5562
```

-continued

```
cctcagcagc cagcgcggct gatgcggttg tggacaatgc cgagaacgcc atcgccgggt    5622
ctgacgtggc gacggtgcat acatattccc tcagggaact tggtgcgcag agtgccctca    5682
aaatgcaggg cgctgctacg ctgcagggcc tgcagttcgg tattccggcc gaccagctcg    5742
tgacttcggc gcggcttgtc gtgtcgggtg cgatgtcgcc cagcctccag cctgacacca    5802
gcgcggtcac gatcacgctg aacgaacagt tcatcggcac gctgcggcct gaccccacac    5862
accctacatt tgggccgctt tcgtttgata tcaacccat cttcttcatc agtggcaacc     5922
ggctgaattt cagcttcgct tcaagctcga agggctgcac ggaccccagc aacgggttgt    5982
tctgggccag cgtgtccgaa cattccgagc tgcagatcac caccatcccg cttccccgc     6042 atcgccagct gtcgcgtctg ccccagccgt tcttcgacaa gaacgtaaag cagaagatcg    6102
tcattccgtt cgttctcgca cagacatttg atcccgaagt gctgaaggcg acgggcatcc    6162
tggcatcgtg gttcggccag cagaccgatt accgtggcgt caccttcccg gtcttctcca    6222
ccattccgca aacgggcaac gccgttgttg tcggcgtggc tgacgagctg ccttccgccc    6282
tcgggcgcca ggcggtcagt ggccccacgc ttatggaagt ggccaatcca tccgacccca    6342
acggcacgat cctgctcgta accgggcgcg accgtgatga agtcatcacc gcgagcaagg    6402
gcatcggttt tggttcgagc accctgccga cagccaaccg catggacgtg cgccgatcg    6462 aggtcggggc ccgcgtggcg aatgacgcgc cctccttcat tccgaccaac cgcccggtcc    6522
gcctgggcga actggtgcca gacagcgccc tgcaggctga aggttacgcc cctggcgcgc    6582
tggcggtgcc attccgtgtc tcgcctgacc tgtatacgtg gcgcgatcgg ccgaacaagc    6642
tgaacgtccg tttccgcgcg ccgccgggc cgatcgtgga tgtgtcgcgc tcgtcgctca     6702
atgtaggcat caacgatacc tatctcgagg cctatccgct gcgtgagccg gattcaccgc    6762
tggaccagct cctgcatggg gtgggccttg gccatcgtaa taatgacagc gtgcagcagc    6822
acaccatgcc catcccgacc taccgggtct ttggccagaa ccagctgctg ttctatttcg    6882
agatggcggc gatggtcgag ccgggctgca aacccggccc gagcacgttc catatgggca    6942
ttgatcccaa ttcgacgatc gatctgtcca actcctatca catcacccag atgcccaacc    7002
tcgccttcat ggccagtgcg ggctttccgt tcaccaccta tgccgacctg tcgcgctcgg    7062
ccgtggtgct gcccgaacac cccaatggca tgattgtcag cgcctatctc gacctcatgg    7122
gcttcatggg ggcgacgaca tggtatccgg tgtctggcgt tgatgtggtc tccagcgacc    7182
atgtgaatga cgtggcggac cggaacctga ttgtcctgtc cacgctggcc aatagcggtg    7242
atgtttcgca gctgctgagc aattcggcct atcagatttc cgatgggcgg ctgcacatgg    7302
ccctgcgttc gacgctgagc ggcgtgtgga acctttccca ggatcccatg tcggccatca    7362
acagcacggc cccgaccgat gtcgagagca cgctgaccgg tggcgtggcc gcgatggtcg    7422
aggcggaatc gccgctggca tcgggtcgga ccgttctcgc gctgctttcg ggtgacgggc    7482 agggggctcaa caaccttgtg cagatcctgg cgcagcggaa aaaccaggcc aagatccagg    7542
gtgatctggt gctggcacat gggatgacc tgacctccta ccgcagctcg ccgctgtata    7602
cggttggcac cgtgccgctg tggctcaagc ctgactggta tatgcacaac catcccagcc    7662
gcgtggtcgt ggttggcctg ttcggttgcc ttctggtggt ggctgtcctg atgcgcgccc    7722
tgaccaagca tgctctgcgc cgccgtcggg agttgcagga agaaaggcag agaacgtgat    7782
catgaacagg cgatacgccc tttcgctttc tggtgccctg ctggccagca gttgcatgac    7842
ggtgctggtg gcggttcctg ttgcgcgggc gcagcaggct tccactgccg tgacttccac    7902
agccgcgagt ccggctgcgg ccccacggca gatcctgttg cagcaggcac gcttctggct    7962
```

```
tcagcagcag caatatgaca atgcccgcca ggccctgcag aatgcgcagc gcatcgcccc    8022
cgatgcccct gacgtgctgg aagtggaggg tgaataccag gcggccgttg caaccgcga     8082 agccgctgcc gataccctgc gccacctgca gcaggtggcc ccggccagca cggcggtcag    8142
caacctgagc gatctgctca gcgagcgggc catttcccaa agcgacctgt cacagatccg    8202
ttcgctggcg ggttcgggcc agaacgcgca ggcggtggcg gggtaccaga agctgttcca    8262
cggtggcaag ccgccccgtt cgcttgcggt ggaatactac cagaccatgg cgggcgtgcc    8322
gacccagtgg gaccaggcgc gcgcggggct ggccgggatc gttgcgtcca acccgcagaa    8382
ttaccgcgcc cagctcgcct ttgcccaggc cctgacctat aatacctcga cccgcatgga    8442
aggcctgacc cggctcaagg atctgcaatc cttccagagt caggccccgg tcgaagctgc    8502
cgccgcgacg cagtcctatc gccagaccct gagctggctg ccggtcaatc ccgatacgca    8562
gcccctcatg gagcagtggc tttccgccca ccccaatgat gccgcgctgc gcgaacacat    8622
gcttcacccc ccggcggcc cgccggacaa agcggggctt gcgcggcagg ccggttacca     8682
gcagctcaac gcgggccgtc tttccgctgc cgaacagtcc ttccagtcgg cgttgcagat    8742
caactcccat gatgctgatt cactgggtgg catgggcctc gtgagcatgc ggcagggcga    8802
taccgccgag gcgcacccct attttgaaga ggcgatggcc gccgacccca agactgccga    8862
tcgctggcgc ccggcgcttg cgggcatggc ggtcagcggg gactatgccg ccgttcgcca    8922
gttgattgcc gccatcagt ataccgaggc caagcagaag cttgccacgc tggcccgcca    8982
gcccgggcag tacaccggcg cgaccctcat gctggccgac ctgcagcgct cgaccgggca    9042
ggttgccgcc gccgagcagg aatatcgtgg catcctgtcg cgtgagccca ataaccagct    9102
ggcccttatg gggctggcgc gggtggacat ggcgcagggc aacacggcgg aagcacgcca    9162
gctcctgtcg cgtgtgagcc cgcaatatgc cagccaggtc ggggaaatcg aggtttccgg    9222
ccttatggcg gcagcgtcgc agacatcgga ttcagcgcgc aaggtttcca tcctgcgcga    9282
agcgatggcc caggccccgc gtgacccgtg ggtgcgcatc aaccttgcca atgcgctgca    9342
gcagcagggc gatgtggctg aagccgggcg cgtgatgcag cccatcctgg ccaatcctgt    9402
caccgcgcag gaccgccagg ccggtatcct gtatacctat ggcagtggca atgatgcgat    9462
gacccgccag cttctggccg gtctgtcgcc cgcggattat tcccccgcga tccgttccat    9522
tgccgaggaa atggaaatca agcaggacct ggccagccgc ctgtcgatgg tatccaaccc    9582
ggtgccgctg atccgcgagg ccctttccca gcctgatccg accggcgcgc gtggcgtggc    9642 ggtgccgac ctgttccgcc agcgtggcga catggtgcat gcgcgcatgg cgctgcgtat     9702
cgcctcgacg cgcaccatcg acctttcgcc cgaccagcgc ctgtcctacg ccaccgaata    9762
catgaagatc agcaacccgg tggcagccgc acgcctgctg gccccgctgg ggatggcac    9822 gggttcgggc gcgggcaatg cgctgctgcc cgagcagatg cagacattgc agcaactgcg    9882
catgggcatc tcggtggcgc agtccgatct gctcaaccag cgtggcgatc aggcgcaggc    9942
ctacgatcat ctggcgcccg ccctgcaggc cgacccggag gcgacatcgc caagctggc    10002 gctcgcgcgg ctgtataacg ccacggcaa gccgggcaag gcgctcgaga tcgaccttgc     10062
ggtgctgcgc acaacccgc aggatcttga tgcgcgcag gcggcggtgc aggcggcggt     10122
caacagcaac cacaacagtc ttgccacccg tctcgcgatg gatggcgtgc aggaaagccc    10182
gatggatgcc cgcgcctggc tggccatggc cgtagctgac caggccgatg gccatggtca    10242
gcgcaccatc gaggacctgc gccgcgccta tgacctgcgc ctgcagcagg tcgagggcac    10302
```

-continued

```
gcgggccgcg tctggtccgg tcggggcgca tgaagaagcg cttgccccgc catcgaccaa    10362
cccgttccag tcgcgtggct acgggcatca ggtggaactg ggcgcgccgg tgaccggtgg    10422
ctcctacagt gccgaggcgg catcgcccga tacgtcggac cagatgctct cctccattgc    10482
tggccagatc cacacgctgc gtgaaaacct tgcaccctcc attgatggtg ggctgggctt    10542
ccggtcgcgt tcgggcgagc atggcatggg ccgcctgacg gaagcgaaca ttcccatcgt    10602
gggccgcctg ccgctgcagg ccggtgcttc cgccctgacc ttctcgatca cgccaaccat    10662
gatctggtcg ggccagctca acacaggctc cgtctatgat gtgccgcgtt atggcacgtt    10722
catggcaacg caggctgcca accagtgcgc gggccacagt tcgtgtggcg ggcttgattt    10782
cctgagcgcc aaccataccc agcgcatcgc ggctggtgca ggcgaggccg ggtttgcgcc    10842
ggatgtgcag ttcggcaata gctgggtgcg cgctgatgtc tgcgcctcgc ccatcggctt    10902
ccccattacc aacgtgctgg gcgggtcga gttctcgccg cgcgtggggc cggtcacgtt    10962
ccgtgtcagc gccgagcgcc ggtcgatcac caacagcgtg ctgtcctatg gtggcctgcg    11022
tgatccgaac tacaacagcg aggtcggtcg ttacgcgcgt caggtctatg gtcatgacct    11082
gaccaagcag tggggtagcg aatggggtgg ggtggtgacc aaccacttcc acggtcaggt    11142
cgaggcgacg ctgggcaaca ccatcctgta tggtggtggc ggctacgcga tccagaccgg    11202
caagaacgtg cagcgcaaca gcgagcgcga agccggcatc ggcgccaata cgctggtgtg    11262
gcataacgcc aacatgctgg tgcgcattgg cgtgagcctg acctatttcg gttatgccca    11322
taacgaggat ttctatacct atgggcaggg cggctacttc tcgccgcagt cctattatgc    11382
ggcaaccgtg ccggtgcgtt atgcgggcca gcacaagcgg ctggactggg atgtgacggg    11442
tagcgtgggc taccaggtgt tccatgaaca cgcggcgccc ttcttcccca cgtcatcgct    11502
gctgcagtcc ggtgccaatt acgttgcatc gaactttgtg cagaatgccc tgccaacgga    11562
ttatctgtcg caggaaacgg tgaacagcgc ctactatccc ggggatagta ttgctggtct    11622
tacgggcggc tttaatgcta gggtgggcta tcgctttaca cgcaatgttc gtcttgatct    11682
ctcggggcgc tatcagaagg ccggtaactg gactgaaagc ggcgccatga tttccgcaca    11742
ctatcttatt atggaccagt aatgacaact ttgaacgcaa aaccggactt ttcgcttttc    11802
ctgcaggcac tgtcctggga gatcgatgat caggccggga tcgaggtcag gaatgacctg    11862
ttgcgcgagg tcggccgggg tatggctggt cgtttccagc cgccgctgtg caacaccatc    11922
caccagctcc agatcgagct gaacgccctg ctggccatga tcaactgggg ctacgtaaag    11982
ctggacctgc tggcggaaga acaggccatg cgcatcgtgc atgaagacct gccgcaggtg    12042
ggcagcgcgg gcgaacccgc cggcacatgg cttgccccgg tgctggaagg gctttatggc    12102
cgctggatca cgtcgcagcc cggcgccttc ggtgattatg tcgtgacgcg tgatatcgac    12162
gcggaagacc tgaactcggt cccggcccag acggtcatcc tgtacatgcg cacccgcagc    12222
gccgcgacct gaccttacca gtcgcgccat ttgcgtcaaa ccctgccca caggcgtgtt    12282
catgcccgtgt aggcggggtt tttgcgtata tggcctccac tctttgccct gttttttgcgc    12342
tagatcatgc ggcgtggggg caggtgcttt cacaaatggg ccaaggagat ggcgggcggc    12402
tgcccgtgtc gtcactgtcc agcccctgaa ggaggagcca gccacatgag actgtcccgc    12462
aagatattcc tgttatccgc cgtggcgtgt ggcatggcgc tggcccaggc gcccgccttt    12522
gcccggcatg cgcatgatgg cggggcgac caggccgatg cccggcgcg gcaggtgctc    12582
gcctccatga gccttgagga caagatgtcc ctgctgttca gtgttgatgg cggcggcttt    12642
aacggcagcg tggcccctcc cggtggcctg gggtcggctg cataccgtgcg cgcgccccag    12702
```

-continued

```
ggttcgggcc tgcctgacct gcagatttcg gatgcggggc ttggcgtgcg caaccccgcg   12762
catatccgca ggaatggtga agcggttttcg ctgccgtcgg gccagtccac ggccagtacg   12822
tgggatatgg acatggcgcg gcaggccggt gtcatgatcg ggcgcgaggc atggcagagc   12882
ggcttcaaca tcctgcttgg cggcggtgcg gacctgacgc gcgacccgcg tggcggccgc   12942
aactttgaat atgcgggcga agatccgctg cagaccgggc gcatggtggg cagcaccatt   13002
gcaggcgtgc agtcgcagca tgtgatctcc acgctcaagc attatgcgat gaatgacctc   13062
gaaacctcgc gcatgaccat gagcgcggat atcgaccctg tggccatgcg tgaaagcgac   13122
ctgctgggct tcgagatcgc gcttgaaacc gggcatccgg gcgcggtcat gtgctcgtac   13182
aaccgcgtca acgacctgta tgcgtgtgaa aacccgtacc tgctgaacaa gacgctgaag   13242
caggactggc attatcccgg ctttgtcatg tccgactggg gggccacgca ttcctccgcg   13302
cgggcggcgc tggcggggct ggatcaggaa tccgcaggtg accatacgga tgcccggccc   13362
tatttccgca ccctgctggc tgctgacgtc aaggccggac gcgtgcccga agcgcgcatc   13422
aacgacatgg cggagcgcgt tgtccgcgcg ctgttcgcgg cggggcttgt ggaccatccg   13482
gcgcagcgcg ggccgcttga tgtcgtgacc gatacccctcg tggcccagaa ggatgaggaa   13542
gaaggcgcgg tcctgctgcg caaccagggc aacatcctgc cgctttcgcc taccgcgcgc   13602
attgccgtca ttggtggcca tgccgatgcg ggcgtgattt cgggcggtgg ctccagccag   13662
gtcgatccca tcggggcga ggcggtgaag gggccgggca agaaggaatg gccgggtgat   13722
ccggtctatt tcccgtcctc gccgctcaag gccatgcagg ccgaggcgcc cggtgcccgg   13782
atcacctatg atcccggcac cagtatcgcc tctgccgtgc gggccgcgcg ggcggctgac   13842
gtggtggtgg tatatgccac gcagttcacc ttcgagggga tggacgcgcc cagcatgcac   13902
cttgatgaca atgccgatgc gctgattacg gccgtggccg ccgccaaccc gcgcacggtg   13962
gtggtgatgg aaaccggcga cccggtgctg atgccgtgga acagcagcgt ggcgggcgtg   14022
ctcgaggcat ggttccccgg ttcgggcggt ggtccggcca ttgcccggct gctgtttggc   14082
aaggttgcgc cctcgggcca cctgaccatg accttcccgc aggcggaatc tcagctggcc   14142
caccccgata ttgcaggtgt tacggcagat aacgtgttcg agatgcagtt ccataccgat   14202
caggaactgg tttacgacga aggcagcgat gtcggttatc gctggttcga ccgcaatcac   14262
ttcaagccgc tctatccgtt cggttatggc ctgacctaca ccacgttcag caccgatggg   14322
ctgaaggtga cggaacgcca tgggcaggtt acggccacgt tcaacgtgca caacaccggc   14382
acgcgggcgg gcgtggatgt tccgcaggtc tatgttggcc tgcccgatgg tggcgcgcgc   14442
cgcctggcgg gctggcagcg catcagcctg cgccgggccg agagccgtca ggtttccgtg   14502
cagcttgagc cgcgcctgct ggcccatttc gatggaaaac atgaccggtg gagcgtgccc   14562
tcgggcacct tccgcgtgtg gcttgcgtca tgcgccaccg atgacagcca gcagaccacc   14622
atgcatctgc atggccggac catggcgccc tgagggtgga tgtcatgggc aggggggtat   14682
gtgtagcggc gatgatgggg gcgggcctgc tgcctgccag ccccatgctg gcggccagcc   14742
tttcatggtc cgatacgcca gccgagcgcg cgcgcctgat gatgagcgtg caggaactgg   14802
aaataaccct gctcacccac cccagcgcca cgctggcgct ggaggactgg tgcgctaccc   14862
accatatggc agcacgcccc gttgtcgtgg cgcagaaggt cgccctgccg cagcccgacc   14922
ccgtgcccgc gcggggtgcgg gccgatctgg cgtgagtgc tgcgcaaccg gtgcggcacc   14982
ggcaggtgcg gctggtctgc gggccatatg tgctttcggt ggcggataac tggtatgtgc   15042
```

-continued

```
ccgccctgct gaccccgcag atgaacgcca cgctggaggg aaccgacaca tccttcggcc    15102
atgtggtggc gccgctgcac tttacgcgcg agcggctgga gtttacgcgg ctgtggtcgc    15162
catggccggg accggttgtg gggcagggcg gcacgatgat cgtggctccg gctgaaatcg    15222
tgcgccagcg cgcggtactg cgtgacggcc agggccgtcc gttcagcgag gtggtggaaa    15282
cctataccga ccagaccctc gcttttacgc ctcaggccga gaggtaaagc tttcctccaa    15342
aaagctttaa agaacgctgc cttttgaaa aaaggcggca cccggaaact tttattctct     15402
gttcccctgc cgtttgcagc ctggcggcag gagggctacg ccggagcatg cgatcatgac    15462
cggagccaga accccatga cagatttgcg agatcccaac acccctgccg agaccgtgcg     15522
gcagctactg ggcctgcaac cccaccccga aggcggcagc taccgcgaac tatggcgcga    15582
taccccgccc gatggcccgc gtggcgcggt ctcgaccatc agtttcctgc tggcggcagg    15642
cgagcgctcg cactggcacc gcgttgatgc agccgagatc tggtgctggc agggtggcgg    15702
cccgcttgtg ctggaaattg ccgcaaggca gggtgccgng atcgagcgga tcgtgcttgg    15762
cccgntgcca gcacgggggc aggtgttgca ggcggtggtg ccaccgggcg catggcaggc    15822
ggctcagagc gaggggggcgt ggagccttat gggctgccag gtggcccccg ccttcgtttt    15882
cagccagttt gaactggccc cgcccggctg acgccacaa ggagacaatg catgacaacc     15942
ccgcaatggc tcatctgggc ccgtgacctg caggcgctgg cccagagcgg cctgacctat    16002
gccgaaagcc cgttcgaccg cgaacgttat gaaagcataa ggcagatcgc agccgatatg    16062
atggccgcgc gcagtcatgc cgacatggag cgcgtgctcg acctgttcac cagtcaggac    16122
ggctatgcca cgcccaagct ggtggtgcgc gccgccgtgt ttgatgcgca gggccgcatg    16182
ctgctggtgc gcgaggtgct ggaccatgac cgctggaccc tgccgggcgg ctgggcggat    16242
gtaaacctga ccccggtgga aaatacggta aaggaagtgc gcgaggaaag cggcttagc     16302
gtgcgcgtga ccaagctcgc cgccgtgtgg gaccgcgacc ggcagggcca tccgcccgca    16362
cccttttcat gctgcacgct ttgtttcatc tgcgaactga ccggtgggag cgccgagacc    16422
agtatcgaga catcggagat tggctggttt gcagccgaca gcctgcctac cgacttgtcg    16482
cttgggcgcg tgctgcccca tcagctgacc cgcatgttag aacatgccgc caaccccgac    16542
ctgcccaggg atttttgatta aaatcgtttta aagacaatgt attggtgaaa gcaggaaagg    16602
ttttttgggtg tcgccttttt tcaaaagggt ggcatttggc caggccggtc agcaagcagt    16662
ctcaccctgc atggcttgcg ggcgctgtgc atgcaggcca ttgaaaaacc gaccgggatt    16722
tccatatcca atacaaattg taacctgatg cagtgcaaca gacagactgg ataagccatg    16782
accgaacaga ccaccacgac cccacccgaa gccacgggcg aacagcatga attc           16836
```

<210> SEQ ID NO: 11
<211> LENGTH: 344
<212> TYPE: PRT
<213> ORGANISM: Acetobacter xylinum
<220> FEATURE:
<223> OTHER INFORMATION: n at positions 15741 and 15767 may be a, g, c, or t

<400> SEQUENCE: 11

Val Ser Thr Pro Glu Lys Glu Ala Gly Thr Gln Val Asn Ile Asp Asn
 1               5                  10                  15

Gln Gln Asp Val Asp Arg Met Leu Thr Asp Gly Tyr Gly Ile Ser Ser
             20                  25                  30

Ala Gly Phe His Tyr Arg Pro Phe Lys Gln Lys Arg Pro Pro Arg Pro
         35                  40                  45

```
Glu Val Arg His Asp Glu Ser Gly Ala Glu Ala Ala Ala Glu
 50                  55                  60

His Ala Pro Ala Ala Glu Glu Ala Ser Gln His Phe Val Ser Ser Tyr
 65                  70                  75                  80

Asp Asp Thr Tyr Ser Thr Pro Ala Ala Pro Glu Ala Ala Pro Val Glu
                 85                  90                  95

Ala Ala Glu Gln Pro Gln His Tyr Gly Glu Thr Ala Tyr Thr Pro Ala
            100                 105                 110

Ala His Asp Ala Tyr Ala Ala Gln Pro Glu Pro Glu Gln Ala Ala Pro
            115                 120                 125

Glu Pro Tyr Val Ala His Asp Asp Thr Pro Ala Ala Glu Pro Glu Thr
            130                 135                 140

Tyr Ala Ala Thr His Ala Glu Thr Val Thr Val Pro Glu Tyr Ala Ala
145                 150                 155                 160

Ala Pro Gln Pro Val Ala Thr Pro Val Pro Pro Gln Pro Ala Pro Val
                165                 170                 175

Ala Pro Val Val Ala Ala Val Ala Gln Pro Val Arg Gln Glu Arg Pro
            180                 185                 190

Ser Leu Ser Pro Val Thr Pro Pro Lys Pro Ala Val Ser Ser Phe Met
            195                 200                 205

Ala Pro Arg Pro Ala Pro Ala Phe Gly Ser Ala Ser Ala Thr Pro Pro
210                 215                 220

Ile Ala Ala Glu Asp Trp Ala Pro Val Pro Lys Ala Gln Gln Gln Arg
225                 230                 235                 240

Gly Gln Arg Leu Thr Gly Pro Gly Phe Phe Gly Ala Gly Ser Glu
            245                 250                 255

Arg Ala Pro Ala Ala Arg Leu Phe Gln Ser Ala Pro Val Ser Arg Pro
            260                 265                 270

Val Ser Lys Pro Val Ser Lys Val Thr Thr Met Thr Lys Val Asp Lys
            275                 280                 285

Ser Ser Pro Asn Asp Ser Gln Ala Gly Arg Pro Ala Pro Thr Asp Asn
            290                 295                 300

Ser Pro Thr Leu Thr Glu Val Phe Met Thr Leu Gly Gly Arg Ala Thr
305                 310                 315                 320

Asp Arg Leu Val Pro Lys Pro Ser Leu Arg Asp Ala Leu Leu Arg Lys
                325                 330                 335

Arg Glu Gly Thr Asn Gly Glu Ser
            340

<210> SEQ ID NO: 12
<211> LENGTH: 29
<212> TYPE: PRT
<213> ORGANISM: Acetobacter xylinum

<400> SEQUENCE: 12

Arg His Ala His Asp Gly Gly Asp Gln Ala Asp Ala Arg Ala Arg
 1               5                  10                  15

Gln Val Leu Ala Ser Met Ser Leu Glu Asp Lys Met Ser
            20                  25
```

GENE, GROUP OF GENES, AND NOVEL β-GLUCLOSIDASE

TECHNICAL FIELD

This invention relates to a gene encoding cellulose synthase complex originating in *Acetobacter xylinum* subsp. *sucrofermentans*, a gene encoding cellulase, a gene encoding β-glucosidase (G3ase), and gene group comprising these genes, as well as a novel β-glucosidase (G3ase) itself.

BACKGROUND ART

It is well known that UDP-glucose is a direct substrate in cellulose biosynthesis of Acetobacter, which is linked together by a membrane protein complex called "cellulose synthase", and released out of cells. This complex has been reported to consist of four proteins encoded by an operon of cellulose synthase gene, being named bcs A, B, C and D, respectively (H. C. Wong, et al., P.N.A.S., Vol.87, pgs.8130–8134 (1990)). Among these genes, bcsA, B and C genes are known to be essential for cellulose synthesis since their destruction would lose cellulose-producing capacity. It has been reported that bcsd gene also plays an important role since its destruction would cause a significant change of the structure of cellulose (I. M. Saxena, et al., J.Bacteriol., Vol.176, pgs.5735–5752 (1994)). Recently, it has been reported that the second cellulose synthase gene operon was obtained (I. M. Saxena, et al., J.Bacteriol., Vol.177, pgs.5276–5283 (1995)).

The cellulose synthase complex needs di-GMP as a cofactor. di-GMP is synthesized by cyclase and a gene encoding this enzyme has also been reported (R. Tal and D. H. Gelfand, PCT WO93/11244 (1994)).

It has been reported that upstream of the cellulose synthase gene operon, there are a cellulase gene(CMCase) and another gene (R. Standal, et al., J. Bacteriol., Vol.176, pgs.665–672 (1994)).

The present inventors have studied the cellulose synthase complex gene operon of Actobacter, and now succeeded in determinating the base sequences of a series of genes comprising a novel cellulose synthase complex gene operon and cellulase gene, which originate in *Acetobacter xylinum* subsp. *sucrofermentans*. According to our examination of the base sequence of a novel gene downstream of the novel cellulose synthase complex gene operon, we have also found that the nobel gene conserves well the sequence/region that are maintained in β-glucosidase of various organisms (Y. Kashiwagi, et al., J.Ferment.Bioeng., Vol.78, pgs.394–398 (1994)) and therefore confirmed that this gene is β-glucosidase.

Further, we have actually purified a protein encoded by the above β-glucosidase gene, and examined its various properties.

DISCLOSURE OF INVENTION

The present invention relates to a gene encoding a protein constituting a cellulose synthase complex originating in *Acetobacter xylinum* subsp. *sucrofermentans*, particularly to a gene encoding a protein having an amino acid sequence represented by one of SEQ ID NO:2~SEQ ID NO:5.

This invention also relates to a gene encoding a variant protein having cellulose synthase activity and having an amino acid sequence that has been partially changed from that represented by one of SEQ ID NO:2~SEQ ID NO:5 by deletion, replacement or addition of one or a few amino acids. The genes of the present invention are therefore not limited to those originating in *Acetobacter xylinum* subsp. *sucrofermentans*.

There may be exemplified as the base sequences of said genes DNA those shown as bcsA, bcsB, bcsC, and bcsD in SEQ ID NO:1. Furthermore, the present invention includes any base sequence or any part thereof prepared by a chemical synthesis and genetic engineering method by taking degeneracy of a genetic codon into consideration, which base sequence encodes the same amino acid sequence.

Also the present invention includes a gene comprising DNA that may hybridize with the above base sequences under stringent conditions, and encode the protein having cellulose synthase activity.

Further, the present invention relates to to a gene encoding cellulose originating in *Acetobacter xylinum* subsp. *sucrofermentans*, particularly to a gene encoding a protein having an amino acid sequence represented by SEQ ID NO:6.

This invention also relates to a gene encoding a variant protein having cellulase activity and having an amino acid sequence that has been partially changed from that represented by SEQ ID NO:6 by deletion, replacement or addition of one or a few amino acids. The gene of the present invention is not limited to that originating in *Acetobacter xylinum* subsp. *sucrofermentans*.

There may be exemplified as the base sequence of said gene's DNA that shown as CMCase in SEQ ID NO:1. Furthermore, the present invention includes any base sequence or any part thereof prepared by a chemical synthesis and genetic engineering method by taking degeneracy of a genetic codon into consideration, which base sequence encodes the same amino acid sequence.

Also the present invention includes a gene comprising DNA that may hybridize with the above base sequences under stringent conditions, and encode the protein having cellulase activity.

Further, the present invention relates to β-glucosidase (G3ase) originating in Acetobacter microorganisms such as *Acetobacter xylinum* subsp. *sucrofermentans*, particularly to a protein having an amino acid sequence represented by SEQ ID NO:7.

The amino acid sequence of this protein is not limited to that of SEQ ID NO:7, but may include that of a variant protein having β-glucosidase activity and having an amino acid sequence that has been partially changed from that represented by SEQ ID NO:7 by deletion, replacement or addition of one or a few amino acids.

This invention also relates to a gene encoding β-glucosidase. One of its example is the base sequence shown as β-glucosidase in SEQ ID NO:1. Furthermore, the present invention includes any base sequence or any part thereof prepared by a chemical synthesis and genetic engineering method by taking degeneracy of a genetic codon into consideration, which encodes the same amino acid sequence.

Also the present invention includes a gene comprising DNA that may hybridize with the above base sequence under stringent conditions, and encode the protein having β-glucosidase activity.

One of the representatives of *Acetobacter xylinum* subsp. *sucrofermentans* of the present invention is BPR 2001, which has been deposited at the National Institute of Bioscience and Human-Technology Agency of Industrial Science and Technology (1-3, Higashi 1-chome, Tsukuba-shi, Ibaraki-ken, 305 Japan) on Feb. 24, 1993 under the accession number FERM P-13466, and then transferred on Feb. 7, 1994 to the deposit under the terms of the Budapest Treaty on the International Recognition of the Deposit of Microorganisms for the Purposes of Patent Procedure and Regulation under the accession number FERM BP-4545.

Other examples of the microorganisms belonging to Acetobacter may be *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; and the like.

The present invention further relates to a gene group comprising the gene (operon) encoding the cellulose synthase complex of the present invention, and the gene encoding β-glucosidase originating in Acetobacter microorganisms downstream (on 3'-terminal side) of the cellulose synthase gene.

The present gene group may include the cellulase gene of the present invention and/or glucanase gene upstream of the cellulose synthase complex gene (operon). The present gene group may include further various structural genes and regulating genes such as a promoter and operator. Each of these genes is separated by an appropriate number of bases apart from the other genes. For example, β-glucosidase gene of BPR 2001 strain is located 214-bp downstream of the gene encoding bcsD of the cellulose synthase complex. One embodiment of the base sequence of the present gene group is shown as SEQ ID NO:1. The genes comprised in said gene group, their locations in the base sequence, and intervals therebetween are shown in FIG. 1.

There exists an open reading frame (ORF2) of another gene between the cellulase gene and the bcsA gene of the cellulose synthase complex in the gene group of SEQ ID NO:1. The amino acid sequence encoded by the ORF2 is shown in SEQ ID NO:11. The function of a protein having this amino acid sequence has not been identified yet. However, it has been reported that the destruction of a gene which is located in the similar position in another bacterium would deteriorate its biosynthesis of cellulose. Accordingly, it is very likely assumed that the gene shown by the ORF2 is involved in the biosynthesis of cellulose.

It is considered that the genes and gene group of the present invention encode a series of enzymes that is essential for the production of the cellulose in Acetobacter, and that the gene group of the present invention may possibly be a transcription unit being regulated by a series of promoters.

The genes and gene group of the present invention may be prepared by methods known to those skilled in the art.

For example, a gene library is prepared from the DNAs of a strain of *Acetobacter xylinum* subsp. *sucrofermentans* by a known method. On the other hand, a primer is synthesized based on the base sequence of the gene encoding a known cellulose synthase. PCR method is then carried out using the above gene library as a template to give the genes of the present invention. The genes of the present invention may be alternatively prepared by a hybridization method using an amplified DNA fragment obtained by the PCR method or a probe DNA prepared based on the base sequence of the above DNA fragment.

Those skilled in the art may easily prepare the genes of the present invention by a chemical synthesis based on the base sequence or amino acid sequence encoded thereby of the genes disclosed in the present specification.

Accordingly, each gene constituting the gene group of the present invention does not necessarily originate in the same microorganism (strain). The gene group of the present invention may therefore be prepared by optionally linking genes by a genetic engineering method, each of which genes has different origins and separately prepared.

Those genes and gene group may be inserted into a host cell such as *E.coli* to produce a series of the genes required for the production of cellulose.

The present invention is therefore related also to an expression vector comprising the gene(s) or the gene group, to a transformed cell such as *E.coli* transformed with the expression vector.

The expression vector of the present invention may optionally comprise an enhancer, promoter, ribosome-binding sequence, signal peptide-encoding sequence, replication origin and gene encoding a selection marker in addition to the above genes and gene group.

The expression vector, the transformed cell, and a series of the enzymes essential for the production of cellulose may be prepared by various genetic engineering methods known to those skilled in the art.

Accordingly, the present invention relates further to the thus prepared recombinant proteins, i.e., the above enzymes.

BEST MODE FOR CARRYING OUT THE INVENTION

Example 1

Preparation of Genes and Determination of Their Sequence

DNA was prepared from BPR 2001 strain according to the method of Murray M. G. & Thonpson W. F. (Nucl.Acids.Res., Vol.8, pgs.4321–4325 (1980)). The resuting DNA was partially digested with a restriction enzyme Sau3AI to give a fragment of about 15–30 kbp. The resulting fragment was then linked with a BamHI-digested fragment of cosmid pHC79 (ATCC37030) with DNA ligase, and was formed into a phage particle using a commercially available DNA in vitro packaging kit (Amersham Co.). *E.coli* was transfected with the particles, inoculated into L-broth containing ampicillin to form colonies. A gene library was thus prepared.

The colonies were transferred onto a nylon membrane (Amersham Co., Hybond-N+) and subjected to bacteriolysis using alkali according to a protocol attached to the kit so that DNA was denatured and fixed on the nylon membrane.

On the other hand, the following two DNA fragments were synthesized based on the known base sequence of cellulose synthase of *Acetobacter xylinum* 1306-3 strain (H. C. Wong, et al., Proc.Natl.Acad.Sci., USA, Vol.87, pgs.8130–8134 (1990)):

ACCGAATGCGTCTGACGGTT SEQ ID NO: 8;

and

TGATGATGGTTACGCGCACC SEQ ID NO. 9.

The PCR reaction was carried out under normal conditions using the above synthesized DNAS as a primer and the DNA prepared from BPR 2001 strain as a template to amplify a DNA fragment which was a part of the cellulose synthase gene. The resulting DNA fragment was isolated and collected by agarose electrophoresis, ans used as a probe.

The nylon menmbrane on which the DNA had been fixed was hybridized with the resulting probe using ECL labelling kit (Amersham Co.) in accordance with its attached protocol. A clone containing a DNA fragment comprising a full length of the cellulose synthase gene was selected from clones with a signal, and named "AM9." This strain has been deposited at the National Institute of Bioscience and Human-Technology Agency of Industrial Science and Technology (1–3, Higashi 1-chome, Tsukuba-shi, Ibaraki-ken, 305 Japan) on Feb. 14, 1997 under the terms of the Budapest Treaty on the International Recognition of the Deposit of Microorganisms for the Purposes of Patent Procedure and Regulation under the accession number FERM BP-5822.

Figure 1:
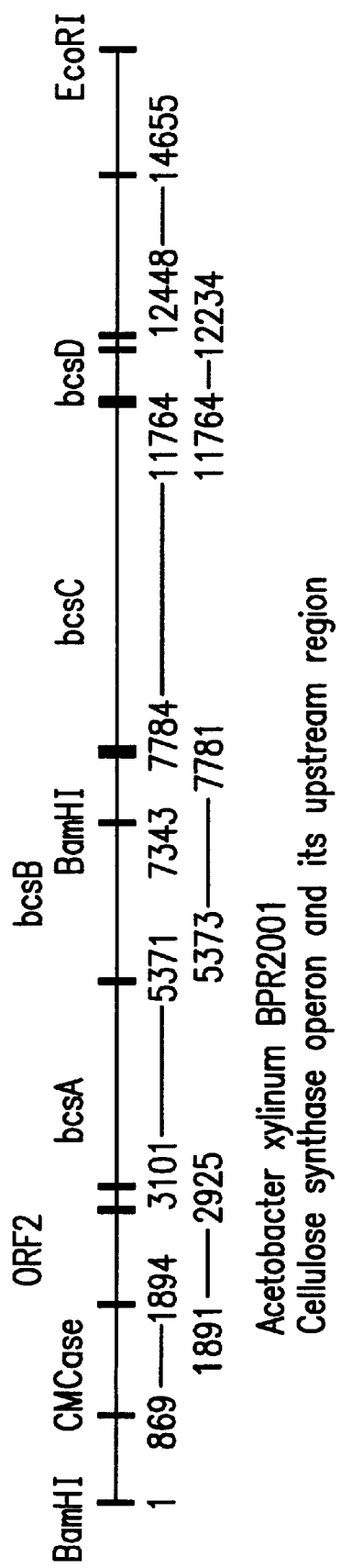
FIG. 1 shows the position in the base sequence of the genes comprised in the present gene group.

A plasmid DNA was prepared from the strain AM9, and its base sequence was determined to confirm that the base sequence of 16.8 kbp was present as shown in FIG. 1.

The examination of the base sequence has revealed the existence of some genes encoding a protein. These genes were then compared with the known base sequences of the other cellulose-producing strains (cellulase and ORF2 disclosed in R.Standel, et al., J.Bacteriol., Vo.176, pgs.665–672 (1994), and cellulose sythase disclosed in H. C. Wong, et al., P.N.A.S., Vol.87, pgs.8130–8134 (1990)) by means of DNA-SIS program (Hitachi Ltd.). The comparison has demonstrated that there is a high homology in DNA and protein between the genes of the strain AM9 and the known genes, showing that the obtained genes correspond to each of the known genes.

TABLE 1

| | HOMOLOGY (%) | |
|---|---|---|
| | DNA | PROTEIN |
| Cellulase | 70 | 69 |
| ORF2 | 38 | 19 |
| bcsA | 92 | 94 |
| bcsB | 62 | 54 |
| bcsC | 83 | 73 |
| bcsD | 96 | 99 |

Homology examination on Gen Bank Base was carried out with respect to a gene existing downstream of the cellulose synthase gene. As a result, it has been revealed that said gene shows as a high homology as 49% in DNA and 33% in protein with β-glucosidase of *Cellvibrio gilvus* (Y. Kashiwagi, et al., J.Ferment.Bioeng., Vol.78, pgs.394–398 (1994)), confirming that the same gene is that of β-glucosidase. A translation starting codon was determined based on the location of Shine-Dalgarno sequence in the DNA base sequence. The location of each gene in the base sequence of SEQ ID NO:1 is shown in Table 2.

TABLE 2

| | Base sequence |
|---|---|
| Cellulase gene | 869–1894(SEQ ID NO: 2) |
| ORF2 gene | 1891–2925(SEQ ID NO: 11) |
| bcsA gene | 3101–5371(SEQ ID NO: 3) |
| bcsB gene | 5373–7781(SEQ ID NO: 4) |

TABLE 2-continued

| | Base sequence |
|---|---|
| bcsC gene | 7784–11764(SEQ ID NO: 5) |
| bcsD gene | 11764–12234(SEQ ID NO: 6) |
| β-glucosidase gene | 12448–14655(SEQ ID NO: 7) |

Example 2

Purification of β-glucosidase (G3ase)

*Acetobacter xylinum* subsp. *sucrofermentans* BPR 2001 strain was cultured in CSL-Fru medium using a jar fermenter (inner volume: 3 L, culture medium volume: 1.8 L) at 30° C. and pH5 for 68 hours. The resulting culture medium (about 8,000 ml in total) was subjected to centrifugation to give its supernatant (3,600 ml). The resulting supernatant was subjected to salting-out with 60%-saturated ammonium sulfate, and the resulting precipitate was collected by centrifugation. The collected precipitate was solubilized into distilled water of 352 ml and dialyzed against distilled water (15 L). The resulting precipitate was collected and extracted three times with 20 mM sodium acetate buffer (pH5.5) containing 0.15 M NaCl. G3ase activity was found in the resulting extract. The extract was subjected to CM-Toyopearl 650M column (Tosoh Co. Ltd.; 3.2 cm in diameter, 13.3 cm in length) equilibrated with 20 mM sodium acetate buffer (pH5.5) containing 0.15 M NaCl to absorb the G3ase activity. A linear gradient in NaCl concentration of from 0.15M to 0.7M was applied to the column so that G3ase was eluted at 0.45–0.55M NaCl. The resulting activity fraction was concentrated by ultrafiltration (Millipore Co., Ultrafree15, fraction molecular weight:5,000), and the resulting concentrate was applied to Toyopearl HW55S column (Toso Co.; 1.5 cm in diameter, 48 cm in length) equilibrated with 20 mM sodium acetate buffer (pH5.5) containing 0.15 M NaCl. To the resulting activity fraction was added NaCl to a final concentration of 1.5M, and the resulting solution was applied to Butyl-Toyopearl 650M column (Tosoh Co. Ltd.; 1.5 cm in diameter, 4 cm in length) equilibrated with 20 mM sodium acetate buffer (pH5.5) containing 1.5 M NaCl, washed with the same buffer, and eluted with 20 mM sodium acetate buffer (pH5.5) containing 1.0 M NaCl. The resulting activity fraction was added to Sephadex G25PD-10 column (pharmacia) for exchange with 20 mM sodium acetate buffer (pH5.5) containing 0.15 M NaCl to give a purified sample. The purified sample was checked to have a singe band on SDS-polyacrylamide electrophresis. Specific activity was 840 U/mg-protein, purification ratio was 337, and recovery ratio was 5.5% based on the total activity of the supernatant (100%).

The activity of β-glucosidase (G3ase) was determined as follows:

An enzyme solution (2 $\mu$l) was mixed with 1% (w/v) cellotriose (G3:Seikagaku Kogyo Ltd.) (2 $\mu$l) and 0.3% (v/v) Triton X-100 (Sigma) (2 $\mu$l). After reaction at 30° C. for 2 hr, a reaction solution (300 $\mu$l) of a glucose-measuring kit (Glucose CII test Wako: Wako Pure Chemical Industries, Ltd.) was added to the mixture, and reacted for 15 min at a room temperature, followed by the determination of an amount of glucose based on absorbance at 505 nm. One activity unit (U) was defined as an amount of the enzyme that could produce 1 $\mu$mol of glucose from G3 at 30° C. for 2 hr.

Example 3

Molecular Weight and Isoelectric Point of the Purified Sample of β-glucosidase (G3ase)

Figure 2:
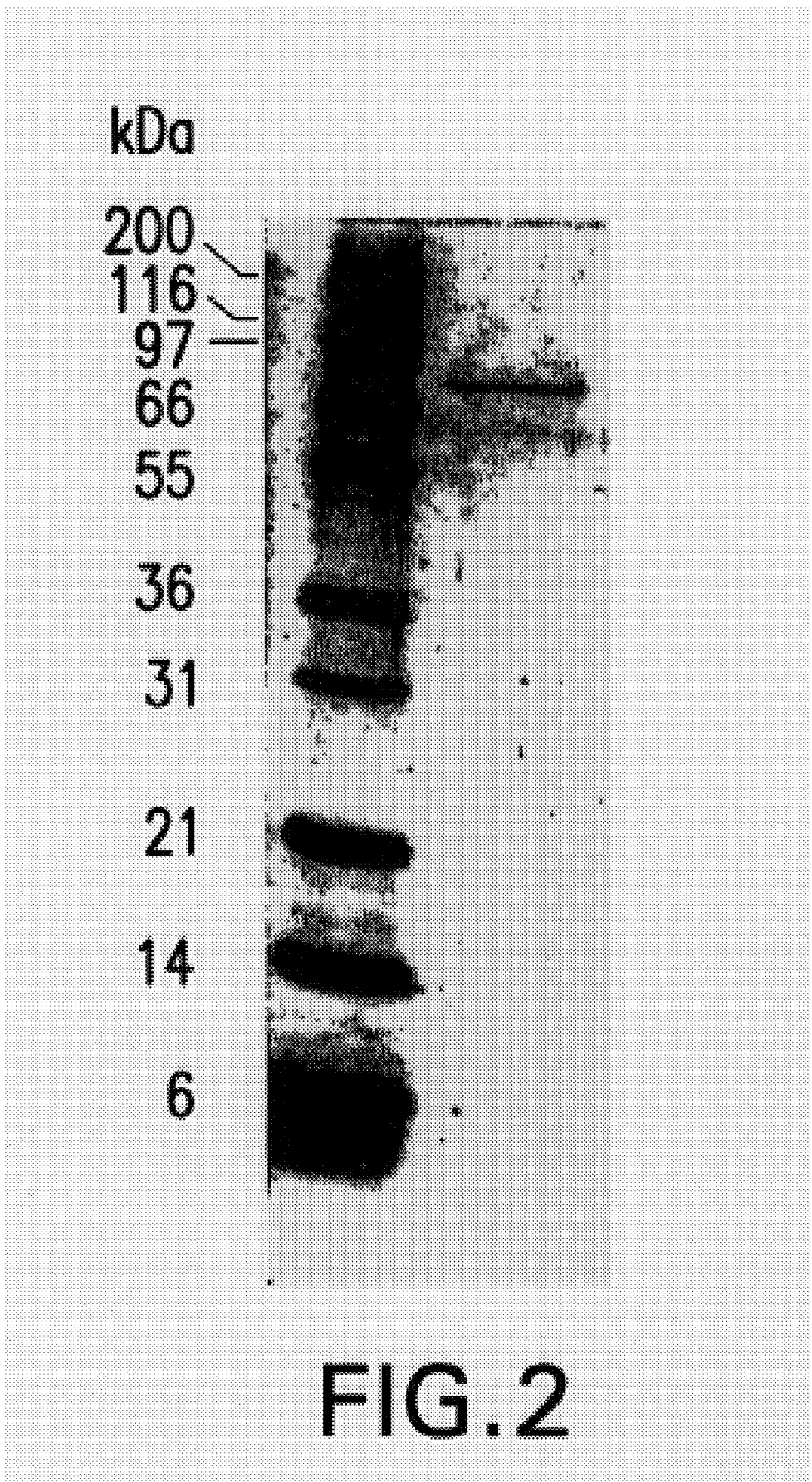
FIG. 2 shows the result obtained with respect to a purified sample of β-glucosidase in SDS-polyacrylamide gel electrophoresis.
Figure 3:
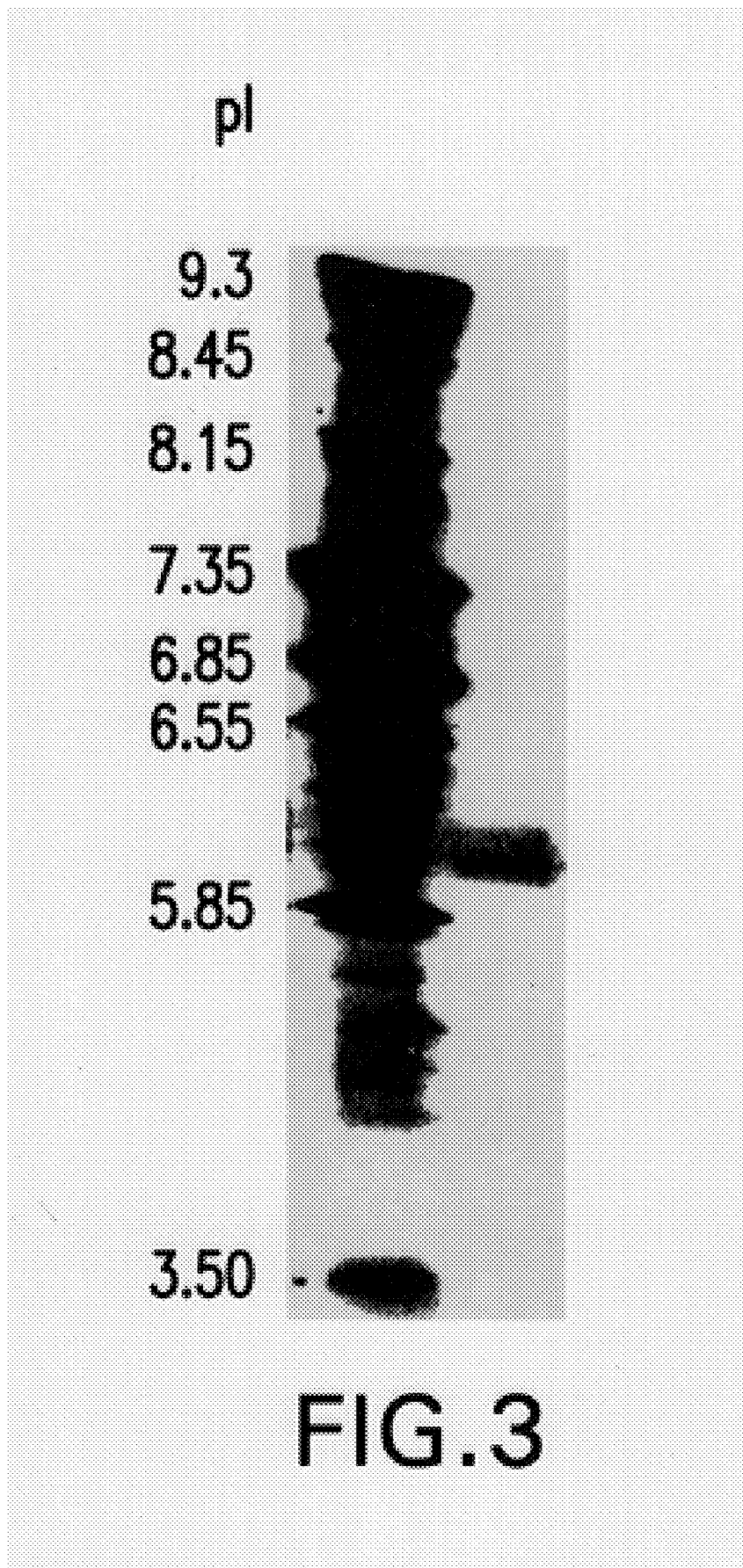
FIG. 3 shows the result obtained with respect to a purified sample of β-glucosidase in electrofocusing SDS-polyacrylamide gel electrophoresis.

The molecular weight of β-glucosidase (G3ase) determined by SDS-PAGE was about 81,200 (FIG. 2). Its isoelectric point (pI) determined by IEF-PAGE was about 6.0 (FIG. 3).

Example 4

N-terminal Amino Acid Sequence of β-glucosidase (G3ase)

β-glucosidase (G3ase) was separated by SDS-PAGE, electrically blotted onto a polyvinylidene difluoride (PVDF) membrane, and stained with Coomassie Brilliant Blue to visualize a band of β-glucosidase (G3ase). The excised band was applied to an automatic amino-acid sequencer (Hewlett Packard Inc., HP G10005A) and its N-termal amino acid sequence has been determined as follows: -RHAHDGGGDQADARARQVLASMSLEDKMS SEQ ID NO:12- (a single character abbreviation for amino acids). This amino acid sequence completely coincides with that from R (arginine) at 27 of the amino acid sequence (SEQ ID NO:7) deduced from β-glucosidase (G3ase) gene represented by SEQ ID NO:1. Thus, it has been revealed that the β-glucosidase (G3ase) gene has a signal sequence of 26 amino acid residues.

Example 5

Effect of pH and Temperature

The pH stability of β-glucosidase (G3ase) was studied. The examination of the remaining activity after 3-hour treatment at 30° C. and various pH values showed that 80% or more activity remained at a pH range of from 3.6 to 7.0 and the enzyme was inactivated at pH 3 or less and at pH 8 or more. An optimum pH was about 5.5. The thermal stability of β-glucosidase (G3ase) was also studied. The examination of the remaining activity after 30-minute treatment at pH 5.5 and various temperatures showed that it was stable at 30° C. or less, but inactivated at 50° C. or more, an optimum temperature being about 40° C.

Example 6

Effect of Metal Ions and Chemical Agent

The effects of metal ions and chemical agents (1 mM) on the β-glucosidase (G3ase) activity were examined, and summarized in Table 3. While Hg++ ion slightly decreased its activity to 85.5% based on a non-added sample (100%), the other ions examined showed no significant effects. On the other hand, NBS (N-bromosuccinimide) completely inactivated β-glucosidase (G3ase). SDS (sodium dodecyl sulfate) also partially (31.3%) inactivated it. But, a SH group-modifying reagent, 2-ME (2-mercaptoethanol), IAA (iodo acetate) and metal-chelating reagent, EDTA (ethylene diamine tetra acetate) did not affect it adversely.

TABLE 3

| Compound(1 mM) | Relative activity(%) |
| --- | --- |
| None | 100 |
| $CaCl_2$ | 100 |
| $MgSO_4$ | 95.2 |
| $ZnSO_4$ | 90.4 |
| $FeSO_4$ | 91.6 |
| $MnSO_4$ | 114.5 |
| $CuSO_4$ | 115.7 |
| $HgCl_2$ | 85.5 |
| EDTA | 100 |
| NBS | 0 |
| IAA | 126.5 |
| SDS | 31.3 |
| 2ME | 106 |

Example 7

Substrate-specificity of β-glucosidase (G3ase)

Reaction parameters (Michaelis constant:Km, Molecular activity: Ko) were determined using cellooligosaccharides (cellobiose(G2), cellotriose (G3), cellotetraose(G4), cellopentaose(G5), cellohexaose(G6)) as a substrate. The results are shown in Table 4. It has been found that β-glucosidase (G3ase) shows a much higher Km for G2 than that for the other substrates, and a much lower Ko for G2 than that of the other substrates. This means that the degrading activity of β-glucosidase (G3ase) is very low for G2 when compared to that for the other cellooligosaccharides. It has also been revealed that this enzyme is competitively inhibited by glucon-o-δ-lactone and conduritol-β epoxide (Table 5). β-glucosidase (G3ase) has a very low degrading activity also for high-molecular weight cellulose substrates such as CMC (carboxy methyl cellulose), lichenan, BC (bacterial cellulose), Avicel, and PRC (phosphate-swollen cellulose) (Table 6).

TABLE 4

Km and Ko of G3ase

| Substrate | $K_m$ (mM) | $k_o$ (sec$^{-1}$) |
| --- | --- | --- |
| G 2 | 221.75 | 3.8 |
| G 3 | 3.73 | 29.8 |
| G 4 | 2.70 | 36.9 |
| G 5 | 1.49 | 32.1 |
| G 6 | 1.31 | 31.0 |

TABLE 5

Inhibitibg constants

| Inhibitor | Ki (mM) | Type |
| --- | --- | --- |
| Glucono - δ - lactone | 0.76 | Competitive |
| Conduritol - β epoxide | 0.00 | Competitive |

TABLE 6

Reactivity with cellulosic substrates

| Substrate | G3ase Reaction time | |
|---|---|---|
| | 2 hr | 24 hr |
| CMC | 0 | 0.1 |
| Lichenan | 0 | 0.2 |
| BC | 0 | 0 |
| Avicel | 0 | 0 |
| PRC | 0.1 | 0.2 |
| Cellobiose | 0.4 | 5.2 |
| Cellotriose | 13.1 | 17.5 |
| Cellohexaose | 24.3 | 28.2 |

The above values show a percent ratio of an amount of the produced glucose against an amount of the total substrate added.

INDUSTRIAL APPLICABILITY

The present inventors have obtained the novel genes and gene group from microorganisms belonging to Acetobacter, which are involved in cellulose synthesis, and have determined their base sequences. These novel genes and gene group are useful in transforming microorganisms by means of genetic engineering and producing cellulose by such transformants.

What is claimed is:

1. A purified polynucleotide comprising at least one polynucleotide encoding a protein having an amino acid sequence selected from the group consisting of SEQ ID NO:3, SEQ ID NO:4, SEQ ID NO:5, SEQ ID NO:6, and enzymatically active fragments SEQ ID NO:4, and SEQ ID NO:5.

2. The purified polynucleotide of claim 1 comprising at least one polynucleotide selected from the group consisting of nucleotides 3101 to 5371 of SEQ ID NO:1, nucleotides 5373 to 7781 of SEQ ID NO:1, nucleotides 7784 to 11764 of SEQ ID NO:1, and nucleotides 11764 to 11234 of SEQ ID NO:1.

3. A purified polynucleotide comprising the nucleotide sequence in SEQ ID NO:1.

4. A vector comprising the purified polynucleotide of claim 3.

5. A purified polynucleotide encoding an isolated protein comprising the amino acid sequence in SEQ ID NO:11.

6. The purified polynucleotide of claim 5 which comprises nucleotides 1891 to 2925 of SEQ ID NO:1.

7. A vector comprising the isolated polynucleotide of claim 6.

8. A purified polynucleotide encoding a protein comprising the amino acid sequence in SEQ ID NO:2.

9. The purified polynucleotide of claim 8, which comprises nucleotides 869 to 1894 of SEQ ID NO:1.

10. The purified polynucleotide of claim 8, wherein said protein has cellulase activity.

11. A vector comprising the purified polynucleotide of claim 8.

12. A purified polynucleotide encoding a protein comprising the amino acid sequence in SEQ ID NO:7.

13. The purified polynucleotide of claim 12, which comprises nucleotides 12448 to 14655 of SEQ ID NO:1.

14. The purified polynucleotide of claim 12, wherein said protein has β-glucosidase activity.

15. A vector comprising the purified polynucleotide of claim 12.

16. A purified polynucleotide comprising at least one polynucleotide encoding a protein having an amino acid sequence selected from the group consisting of SEQ ID NO:3, SEQ ID NO:4, SEQ ID NO:5, SEQ ID NO:6, and at least one polynucleotide sequence encoding a protein with the amino acid sequence in SEQ ID NO:7, SEQ ID NO:11, and SEQ ID NO:2.

* * * * *

UNITED STATES PATENT AND TRADEMARK OFFICE
CERTIFICATE OF CORRECTION

PATENT NO.    : 6,316,251 B1
DATED         : November 13, 2001
INVENTOR(S)   : Tonouchi et al.

It is certified that error appears in the above-identified patent and that said Letters Patent is hereby corrected as shown below:

<u>Title page, Item [54], and Column 1, line 3,</u>
The title should be:
-- [54] GENE, GROUP OF GENES, AND NOVEL BETA-GLUCODASE --

Signed and Sealed this

Ninth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,316,251 B1
DATED         : November 13, 2001
INVENTOR(S)   : Tonouchi et al.

It is certified that error appears in the above-identified patent and that said Letters Patent is hereby corrected as shown below:

<u>Title page, Item [54] and Column 1, line 3,</u>
The title should be:
-- [54] GENE, GROUP OF GENES, AND NOVEL BETA-GLUCOSIDASE --

This certificate supersedes Certificate of Correction issued July 9, 2002.

Signed and Sealed this

Fifth Day of November, 2002

*Attest:*

JAMES E. ROGAN
*Attesting Officer*    *Director of the United States Patent and Trademark Office*